United States Patent
Lemoine et al.

(10) Patent No.: US 7,098,313 B2
(45) Date of Patent: Aug. 29, 2006

(54) DNA SEQUENCES CODING FOR A POLYOL CARRIER AND THEIR USE, IN PARTICULAR FOR THE PREPARATION OF TRANSGENIC PLANTS

(75) Inventors: Rémi René Paul Lemoine, Poitiers (FR); Nathalie Elisane Jacqueline Noiraud, Saint Hilaire la Palud (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 10/332,815

(22) PCT Filed: Jun. 22, 2001

(86) PCT No.: PCT/FR01/01979

§ 371 (c)(1),
(2), (4) Date: Aug. 30, 2004

(87) PCT Pub. No.: WO02/04647

PCT Pub. Date: Jan. 17, 2002

(65) Prior Publication Data

US 2005/0015832 A1    Jan. 20, 2005

(30) Foreign Application Priority Data

Jul. 11, 2000    (FR) .................................. 00 09032

(51) Int. Cl.
*C07K 14/415*    (2006.01)
(52) U.S. Cl. .................................................... 530/350
(58) Field of Classification Search .................... None
See application file for complete search history.

(56) References Cited

U.S. PATENT DOCUMENTS 6,383,776 B1 *    5/2002    Allen et al. ................. 435/69.1

FOREIGN PATENT DOCUMENTS

| EP | 1 033 405 | 9/2000 |
| WO | WO 92/19731 | 11/1992 |
| WO | WO 97/26365 | 7/1997 |

OTHER PUBLICATIONS

Mayer et al., "Sequence and analysis of chromosome 4 of the plant *Arabidopsis thaliana*," Nature, vol. 402, Dec. 16, 1999, pp. 769-777.*
Sato et al., "Structural Analysis of *Arabidopsis thaliana* Chromosome 3. I. Sequence Features of the Regions of 4,504,864 bp Covered by Sixty P1 and TAC Clones," DNA Research, vol. 7, pp. 131-135, 2000.*

Sequence search results showing alignments between SEQ ID No. 2 and sequence of Chiou et al. (listed first on PTO-1449 filed Jan. 13, 2003).*
Tzvy-Jen Chiou et al.: ":Molecular cloning, immunochemical localization to the vacuole, and expression in transgenic yeast and tobacco of a putative sugar transporter from sugar beet", Plant Physiology (Rockville), vol. 110, No. 2, 1996, pp. 511-520, XP002164317, ISSN: 0032-0889.
XP002164320, Database EMBL, Mar. 2, 1996, *Beta vulgaris* integral membrane protein Mrna, complete cds.
T.-J. Chiou et al., Isolation and molecular characteristics of two putative sugar transporters from sugar beet (Accession Nos. U64902 and U64903, PGR97-017, Plant Gene Register PGR97-017, 1997, XP002164318.
Database EMBL, Accession No. U64903, Jan. 21, 1997, T.-J. Chiou et al., "*Beta vulgaris* putative sugar transporter (BvcDNA-397), mRNA, complete cds.", XP002164321.
Database EMBL Accession No. U64902, Jan. 21, 1997, T.-J. Chiou et al., "*Beta vulgaris* putative sugar transporter (BvcDNA-205), mRNA, compleate cds.", XP002164322.
Database EMBL Accession No. Z99708, Oct. 2, 1997, M. Bevan et al., "*Arabidopsis thaliana* DNA chromosome 4, ESSA I AP2 contig fragment No. 2", XP002164323.
Database TREMBL Accession No. 023213, Jan. 1, 1998, M Bevan et al., "Myo-Inositol Transport Protein Homolog (Sugar Transporter Like Protein)", XP002164324.
Database EMBL, Accession No. AL161589, Mar. 16, 2000, H. Hilbert et al., "*Arabidopsis thaliana* DNA chromosome 4, contig fragment No. 85" XP002164325.
Database EMBL Accession No. AC007134, Mar. 24, 1999, X. Lin et al.: "*Arabidopsis thaliana* chromosome II section 93 of 255 of the complete sequence. Sequence from clones F7H1", XP002164326.
Database EMBL Accession No. AC006135, Dec. 7, 1998, X. Lin et al.: "*Arabidopsis thaliana* chromosome II section 108 of 255 of the complete sequence. Sequence from clones F24H14, MSF3.", XP002164327.
Database EMBL Accesion No. AB026654, May 7, 1999, S. Sato et al., "*Arabidopsis thaliana* genomic DNA, chromosome 3, P1 clone: MVE11.", XP002164328.
Database EMBL Accession No. AC006234, Dec. 21, 1998, X. Lin et al., "*Arabidopsis thaliana* chromosome II section 119 of 255 of the complete sequence. Sequence from clones F5H14, F26H11", XP002164329.

(Continued)

*Primary Examiner*—Robert A. Wax
(74) *Attorney, Agent, or Firm*—Young & Thompson

(57) ABSTRACT

The invention concerns the use of a DNA sequence coding for a polyol carrier, in plants and fungi, such as polyols having a main chain containing 5 to 8 carbon atoms, in particular 5 to 7 carbon atoms, more preferably 6 carbon atoms, the polyols being advantageously selected among mannitol, sorbitol, dulcitol, galactitol, inositol, myo-inositol, ribitol and xylitol, and being preferably mannitol, for preparing transgenic plants.

2 Claims, 2 Drawing Sheets

OTHER PUBLICATIONS

Database EMBL Accession No. Z92954, Mar. 17, 1997, C. LeLong et al., "*B. subtilis* yws (A,B,C,D,E,F,G) and gerBC genes", XP002164330.

Database Tremble Accession No. P96742, May 1, 1997, C. LeLong, "Similar to Metabolite Transport Proteins" XP002164331.

Tzvy-Jen Chiou et al., "Immunochemical characterization of three sugar transporters in sugar beet and their expression in transgenic tobacco and yeast", Plant Physiology (Rockville), vol. 105, No. 1 Suppl., 1994, p. 149 XP002164319, Annual Meeting of the American Society of Plant Physiologists; Portland, Oregon, USA; Jul. 30-Aug. 3, 1994, ISSN: 0032-0889.

Nathalie Noiraud et al., "Identification of a mannitol transporter, AgMaT1, in celery phloem", Plant Cell, vol. 13, No. 3, Mar. 2001, pp. 695-705, XP002179565, ISSN: 1040-4651.

Nathalie Noiraud et al., "The sucrose transporter of celery. Identification and expression during salt stress", Plant Physiology (Rockville), vol. 122, No. 4, Apr. 2000, pp. 1447-1455, XP002179580, ISSN: 0032-0889.

Database Biosis Biosciences Information Service, Philadelphia, PA, US; Aug. 1998, Helen Greutert et al., "Mannitol transport by vacuoles of storage parenchyma of celery petioles operates by facilitated diffusion", Database accession No. PREV199800486587, XP002164333.

Database Biosis Biosciences Information Service, Philadelphia, PA, US; 1995, Sandrine Salmon et al.: "Study of sucrose and mannitol transport in plasma-membrane vesicles form phloem and non-phloem tissues of celery (*Apium graveolens* L. petioles", Database accession No. PREV199598523669, XP002164334.

\* cited by examiner

DNA SEQUENCES CODING FOR A POLYOL CARRIER AND THEIR USE, IN PARTICULAR FOR THE PREPARATION OF TRANSGENIC PLANTS

The invention relates to DNA sequences coding for a polyol carrier and their use, in particular for the preparation of transgenic plants.

The plants are capable of synthesizing, via photosynthesis, primary compounds such as glucides by using light energy. Only certain organs of the plant, mainly the adult leaves, are capable of manufacturing and exporting the glucides towards the storage organs, such as the tubers, the seeds and the fruits, used in human and animal foodstuffs.

In the majority of plants, the main glucide transported is saccharose, but in a large number of plants, other compounds are also transported such as polyols of which mannitol is an example.

Polyols are, like saccharose, primary products of photosynthesis. It has furthermore been estimated that approximately 30% of the global production of primary carbon was used for the synthesis of polyols.

Polyols, cyclic or non-cyclic, are very widespread in plants; they are low-molecular weight, very soluble and non-reducing compounds. The three non-cyclic polyols (alditols) which are most widespread amongst the Angiosperms are galactitol, sorbitol and mannitol. Sorbitol is the main photosynthetic product in several species of *Rosaceae* such as the apple, the pear, the peach and the plum.

Mannitol, the most widespread of the alditols, is present in more than 100 species of higher plants, in particular in the *Rubiaceae* (coffee), the *Oleaceae* (privet, ash, olive) and the *Apiaceae* (celery, carrot, parsley) (Lewis, 1984). It is produced in the mesophyll cells (cells containing chlorophyll). To circulate, it must re-enter the sieve tubes (veins). However, there is no continuity between the mesophyll cells and the sieve tubes: a mannitol carrier is therefore needed. In this way, the mannitol leaves the mesophyll cells and uses the carrier to enter the sieve tubes.

The compounds synthesized in the adult leaves are transported towards the storage organs and cross a certain number of membranes using the specialized proteins that are the carriers. These carriers play a considerable role in the plant as they are essential for its growth.

The existence of a mannitol carrier in a plant such as celery has been shown by different biochemical experiments (Salmon et al., 1995). This publication has shown that there was a mannitol carrier in celery and that the expression of this carrier was very sizeable in the tissues of the phloem. However, nothing is said as to the identification of the mannitol carrier.

If numerous carriers of sugars, such as saccharose and the hexoses have been cloned during the course of the last few years, none of them is capable of transporting polyol.

At present, no carrier of linear polyol has been identified in a living organism. In bacteria, a multienzymatic system capable of both transporting and phosphorylating mannitol has been described (Boer et al., 1994). However, such systems have never been described in the higher organisms.

A subject of the invention is carriers of polyols in plants and fungi, and their DNA sequences.

A subject of the invention is also the use of DNA sequences of a polyol carrier for obtaining transgenic plants.

A subject of the invention is also the use of DNA sequences of a polyol carrier, in particular within the scope of obtaining plants resistant to pathogens or plants resistant to saline stress.

A subject of the invention is also the use of DNA sequences of a polyol carrier within the scope of a method of screening genetically modified plants.

The invention relates to the use of a DNA sequence coding for a linear polyol carrier, in plants and fungi, such as polyols having a main chain containing 5 to 8 carbon atoms, in particular 5 to 7 carbon atoms, in particular 6 carbon atoms, these polyols being advantageously chosen from mannitol, sorbitol, dulcitol, galactitol, inositol, ribitol and xylitol, and being in particular mannitol, for the preparation of transgenic plants.

In the expression "plants and fungi", are included algae, mosses (Bryophytes), ferns (Pteridophytes), higher plants (Gymnosperms and Angiosperms) and fungi.

It can be recalled that, by definition, a polyol is a "polyalcohol" containing as many alcohol functions as carbon atoms. It can also be specified that the terms polyol, polyalcohol and alcohol sugar are equivalents.

According to an advantageous embodiment, the invention relates to the use, for the preparation of transgenic plants, of a DNA sequence chosen from one of the following sequences: SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

SEQ ID NO: 1 is a new nucleic acid sequence identified in celery (*Apium graveolens* L.), coding for a mannitol carrier.

SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10 are sequences of nucleic acids coding for proteins, the functions of which were unknown until now.

SEQ ID NO: 3 (Beet 1) and SEQ ID NO: 4 (Beet 2) originate from the Beetroot (*Beta vulgaris*).

SEQ ID NO: 5 (Pst 1), SEQ ID NO: 6 (Pst 2), SEQ ID NO: 7 (Pst 3), SEQ ID NO: 8 (Pst 4) and SEQ ID NO: 9 (Pst 5) originate from *Arabidopsis thaliana*.

SEQ ID NO: 10 (Bs) originates from *Bacillus subtilis*.

The invention also relates to a new protein, characterized by the fact that it comprises or is constituted by:

sequence SEQ ID NO: 2,
  or any sequence derived from SEQ ID NO: 2, in particular by substitution, suppression or addition of one or more amino acids, having the property of transporting linear polyols in plants and fungi, such as polyols having a main chain containing 5 to 8 carbon atoms, in particular 5 to 7 carbon atoms, in particular 6 carbon atoms, these polyols being advantageously chosen from mannitol, sorbitol, dulcitol, galactitol, inositol, ribitol and xylitol, and being in particular mannitol, any homologous sequence of SEQ ID NO: 2, preferably having a homology of at least approximately 50% with sequence SEQ ID NO: 2 and possessing the property of transporting, in plants and fungi, polyols as defined above, or any fragment of one of the sequences defined above, on the condition that it has the property of transporting, in plants and fungi, polyols as defined above, in particular any fragment being constituted of at least approximately 10 amino acids adjacent in the sequence SEQ ID NO: 2.

The property of transporting polyols presented by a polyol carrier can be verified by one or other of the following tests:
  the use of *S. cerevisiae* yeast or
  the use of purified plasmic membrane of phloem vesicles.

The use of the yeast *Saccharomyces cerevisiae* (Noiraud et al., 2000) comprises the transformation of yeasts with the nucleotide sequence to be tested, these yeasts are capable of growing on said polyol. To verify that the polyol is transported in these yeasts, radioactively labelled polyol can be used. For each experiment, a control is perfected with a strain of yeast incapable of growing on the polyol, and which does not transport said polyol.

The test using a purified plasmic membrane from phloem vesicles is that described by Salmon et al. (1995).

According to an advantageous embodiment of the invention, the protein of the invention, as defined above, is characterized in that it is constituted by the sequence SEQ ID NO: 2.

The invention also relates to the protein fragments as defined above, chosen from the following sequences:

Ala Cys Ala Leu Leu Ala Ser Met Asn Ser Ile Leu Leu Gly Tyr Asp Thr Gly Val Leu Ser Gly Ala Ser Ile (SEQ ID NO: 11) delimited from the amino acid in position (26) to the amino acid in position (50) of the sequence SEQ ID NO: 2, Gln Ile Glu Ile Ile Ile Gly Ile Ile Asn Ile Tyr Ser Leu Leu Gly Ser Ala Ile Ala Gly (SEQ ID NO: 12) delimited from the amino acid in position (62) to the amino acid in position (82) of the sequence SEQ ID NO: 2, Tyr Thr Met Val Leu Ala Gly Ile Ile Phe Phe Leu Gly Ala Ile Phe Met Gly Leu Ala (SEQ ID NO: 13) delimited from the amino acid in position (92) to the amino acid in position (111) of the sequence SEQ ID NO: 2, Phe Leu Met Phe Gly Arg Phe Val Ala Gly Ile Gly Val Gly Tyr Ala Met Met Ile Ala Pro Val Tyr Thr Ala (SEQ ID NO: 14) delimited from the amino acid in position (116) to the amino acid in position (140) of the sequence SEQ ID NO: 2, Phe Leu Thr Ser Phe Pro Glu Val Phe Ile Asn Ser Gly Val Leu Leu Gly Tyr Val Ser Asn Phe Ala Phe Ala (SEQ ID NO: 15) delimited from the amino acid in position (150) to the amino acid in position (174) of the sequence SEQ ID NO: 2, Ile Met Leu Gly Ile Gly Ala Phe Pro Ser Val Ala Leu Ala Ile Ile Val Leu Tyr Met (SEQ ID NO: 16) delimited from the amino acid in position (184) to the amino acid in position (203) of the sequence SEQ ID NO: 2, Ala Ala Ile Thr Gly Ile Gly Ile His Phe Phe Gln Gln Ala Cys Gly Ile Asp Ala Val Val Leu (SEQ ID NO: 17) delimited from the amino acid in position (281) to the amino acid in position (302) of the sequence SEQ ID NO: 2, Leu Leu Ala Thr Ile Ala Val Gly Val Cys Lys Thr Val Phe Ile Leu Ile Ser Thr Phe (SEQ ID NO: 18) delimited from the amino acid in position (320) to the amino acid in position (339) of the sequence SEQ ID NO: 2, Leu Met Leu Thr Ser Met Gly Gly Met Val Ile Ala Leu Phe Val Leu Ala Gly Ser Leu Thr Val (SEQ ID NO: 19) delimited from the amino acid in position (349) to the amino acid in position (370) of the sequence SEQ ID NO: 2, Gly Gly Leu Ala Ile Phe Thr Val Tyr Ala Phe Val Ser Ile Phe Ser Ser Gly Met Gly Pro Ile Ala Trp Val Tyr (SEQ ID NO: 20) delimited from the amino acid in position (382) to the amino acid in position (407) of the sequence SEQ ID NO: 2, Cys Ser Ile Gly Val Ala Val Asn Arg Gly Met Ser Gly Ile Ile Gly Met Thr Phe Ile Ser (SEQ ID NO: 21) delimited from the amino acid in position (421) to the amino acid in position (441) of the sequence SEQ ID NO: 2, and Ala Phe Leu Leu Phe Ala Val Val Ala Ser Ile Gly Trp Val Phe Met Tyr Thr Met Phe (SEQ ID NO: 22) delimited from the amino acid in position (451) to the amino acid in position (470) of the sequence SEQ ID NO: 2.

The invention also relates to a nucleotide sequence coding for a protein as defined above.

An advantageous DNA sequence of the invention comprises or is constituted by:

the nucleotide sequence SEQ ID NO: 1, or any nucleotide sequence derived by degeneration of the genetic code, of the sequence SEQ ID NO: 1 coding for a protein represented by SEQ ID NO: 2, or any nucleotide sequence derived, in particular by substitution, suppression or addition of one or more nucleotides, of the sequence SEQ ID NO: 1 coding for a protein derived from SEQ ID NO: 2, as defined above, or any homologous nucleotide sequence of SEQ ID NO: 1, preferably having a homology of at least approximately 35% with the sequence SEQ ID NO: 1 coding for a homologous protein of SEQ ID NO: 2, as defined above, or any fragment of the nucleotide sequence SEQ ID NO: 1 or of the nucleotide sequences defined above, said fragment being preferably constituted of at least approximately 30 nucleotides adjacent in said sequence, or any complementary nucleotide sequence of the abovementioned sequences or fragments, or any nucleotide sequence capable of hybridizing in stringent conditions with the complementary sequence of one of the abovementioned sequences or fragments.

By stringent conditions of hybridization is understood:
temperature of hybridization: 65° C.,
hybridization medium: sodium phosphate buffer 250 mM, pH 7.2; 6.6% (w/v) of SDS; 1 mM EDTA; 1% (w/v) of bovine serum albumin,
washing temperature: 65° C.,
successive rinsing media:
2×SSC (1.75% NaCl; 0.88% sodium citrate), SDS 0.1%
1×SSC (0.875% NaCl; 0.44% sodium citrate), SDS 0.1%
0.5×SSC (0.44% NaCl; 0.22% sodium citrate), SDS 0.1%.

The invention also relates to the fragments of nucleotide sequences as defined above, chosen from the following sequences:

GCT TGT GCT CTT TTA GCT TCC ATG AAT TCC ATC TTA CTC GGC TAT GAC ACC GGA GTG TTG AGT GGA GCA TCA ATA (SEQ ID NO: 23) delimited from the nucleotide in position (92) to the nucleotide in position (166) of the sequence SEQ ID NO: 1, CAA ATC GAA ATA ATC ATC GGA ATC ATC AAC ATC TAC TCT CTT CTT GGT TCG GCC ATA GCC GGA (SEQ ID NO: 24) delimited from the nucleotide in position (200) to the nucleotide in position (262) of the sequence SEQ ID NO: 1, TAC ACC ATG GTA CTA GCT GGT ATC ATA TTT TTT CTA GGA GCC ATT TTC ATG GGG CTT GCT (SEQ ID NO: 25) delimited from the nucleotide in position (290) to the nucleotide in position (349) of the sequence SEQ ID NO: 1, TTT CTC ATG TTT GGT CGC TTT GTT GCT GGA ATT GGT GTC GGT TAT GCC ATG ATG ATC GCT CCC GTC TAC ACT GCC (SEQ ID NO: 26) delimited from the nucleotide in position (362) to the nucleotide in position (436) of the sequence SEQ ID NO: 1, TTC CTC ACT TCT TTT CCT GAG GTT TTC ATT AAT TCT GGT GTG TTG CTC GGG TAT GTA TCC AAC TTT GCA TTT GCC (SEQ ID NO: 27) delimited from the nucleotide in position (464) to the nucleotide in position (538) of the sequence SEQ ID NO: 1, ATT ATG CTG GGA ATT GGA GCA TTT CCT TCA GTT GCC TTG GCC ATA ATT GTG TTA TAT ATG (SEQ ID NO: 28) delimited from the nucleotide in position (566) to the nucleotide in position (625) of the sequence SEQ ID NO: 1, GCT GCA ATT ACG GGT ATT GGT ATT CAT TTC TTC CAA CAG GCT TGT GGT ATT GAT GCT GTT GTT TTA (SEQ ID NO: 29) delimited from the nucleotide in position (857) to the nucleotide in position (922) of the sequence SEQ ID NO: 1, CTC CTT GCG ACA ATT GCT GTT GGA GTC TGC AAA ACA GTC TTT ATT CTG ATA TCA ACG TTT (SEQ ID NO: 30) delimited from the nucleotide in position (974) to the nucleotide in position (1033) of the sequence SEQ ID NO: 1, CTG ATG CTA ACA AGT ATG GGG GGT ATG GTT ATT GCT CTA TTT GTA CTG GCA GGC TCA TTG ACG GTT (SEQ ID NO: 31) delimited from the nucleotide in position (1061) to the nucleotide in position (1126) of the sequence SEQ ID NO: 1, GGT GGT TTG GCA ATA TTT ACA GTG TAT GCT TTT GTG TCG ATA TTT TCA AGT GGC ATG GGT CCA ATT GCT TGG GTC TAT (SEQ ID NO: 32) delimited from the nucleotide in position (1160) to the nucleotide in position (1237) of the sequence SEQ ID NO: 1, TGT AGT ATC GGA GTG GCA GTT AAC CGT GGC ATG AGT GGC ATA ATT GGA ATG ACA TTT ATA TCG (SEQ ID NO: 33) delimited from the nucleotide in position (1277) to the nucleotide in position (1339) of the sequence SEQ ID NO: 1, GCA TTC CTT TTA TTT GCT GTG GTT GCA TCT ATC GGA TGG GTC TTT ATG TAC ACA ATG TTC (SEQ ID NO: 34) delimited from the nucleotide in position (1367) to the nucleotide in position (1426) of the sequence SEQ ID NO: 1, The nucleic acid sequence SEQ ID NO: 23 codes for the protein fragment SEQ ID NO: 11.

The nucleic acid sequence SEQ ID NO: 24 codes for the protein fragment SEQ ID NO: 12.

The nucleic acid sequence SEQ ID NO: 25 codes for the protein fragment SEQ ID NO: 13.

The nucleic acid sequence SEQ ID NO: 26 codes for the protein fragment SEQ ID NO: 14.

The nucleic acid sequence SEQ ID NO: 27 codes for the protein fragment SEQ ID NO: 15.

The nucleic acid sequence SEQ ID NO: 28 codes for the protein fragment SEQ ID NO: 16.

The nucleic acid sequence SEQ ID NO: 29 codes for the protein fragment SEQ ID NO: 17.

The nucleic acid sequence SEQ ID NO: 30 codes for the protein fragment SEQ ID NO: 18.

The nucleic acid sequence SEQ ID NO: 31 codes for the protein fragment SEQ ID NO: 19.

The nucleic acid sequence SEQ ID NO: 32 codes for the protein fragment SEQ ID NO: 20.

The nucleic acid sequence SEQ ID NO: 33 codes for the protein fragment SEQ ID NO: 21.

The nucleic acid sequence SEQ ID NO: 34 codes for the protein fragment SEQ ID NO: 22.

The invention also relates to a recombinant vector, in particular plasmid, cosmid, phage or virus DNA, containing a nucleotide sequence as mentioned above.

The invention also relates to a recombinant vector as defined above, containing the elements necessary for expression in a host cell of polypeptides coded by the nucleic acids as defined above, inserted into said vector.

According to an advantageous embodiment of the invention, the recombinant vector defined above contains in particular a promoter recognized by the RNA polymerase of the host cell, in particular an inducible promoter and optionally a transcription or termination sequence, and optionally a signal and/or anchoring sequence.

According to another advantageous embodiment of the invention, the recombinant vector, such as defined above, contains the elements which allow the expression of a nucleotide sequence, as defined above, as a mature protein or fusion protein.

The invention also relates to a host cell, chosen in particular from bacteria, viruses, yeasts, fungi, plants or the cells of mammals, said host cell being transformed, in particular using a recombinant vector as defined above.

According to an advantageous embodiment of the invention, the host cell, as defined above, contains the regulation elements allowing the expression of the nucleotide sequence as defined above.

The invention also relates to the product of the expression of a nucleic acid expressed by a host cell transformed as defined above.

The invention also relates to an antibody characterized in that it is directed in a specific manner against a protein of the invention.

The invention is not limited to polyclonal antibodies; the invention also relates to any monoclonal antibody produced by any hybridoma capable of being formed according to standard methods starting from, on the one hand, animal, in particular mouse or rat, spleen cells, the cells of the animal being immunized against the protein of the invention, and on the other hand cells of a cell line of myeloma, said hybridoma being capable of being chosen according to the capacity of the cell line to produce monoclonal antibodies recognizing the protein used beforehand for the immunization of the animals.

The invention also relates to a nucleotide probe capable of hybridizing with any one of the nucleic sequences of the invention.

The invention also relates to the antisense oligonucleotides or antisense messenger RNA, derived from the nucleotide sequences as defined above.

By modification of the expression of the mannitol carrier, using antisense oligonucleotides, it can then be determined if a reduction of the expression of the mannitol carrier has the result of reducing tolerance to saline stress.

The invention also relates to plant cells containing in their genome a nucleotide sequence as defined above.

The invention also relates to the transgenic plants, parts of plants, plant seeds or plant propagation material containing cells such as defined above.

The invention relates in particular to transgenic plants which, in their native state, do not contain or express the gene of the mannitol carrier, in the genome of which said nucleotide sequence is introduced.

The invention relates in particular to the transgenic plants which, in their native state, contain or express the gene of the mannitol carrier, in the genome of which said nucleotide sequence is introduced.

The invention also relates to a process for the preparation of a recombinant protein as defined above, comprising the following stages:

Culture in an appropriate medium of a host cell which has been transformed beforehand by an appropriate vector containing a nucleic acid of the invention, and Recovery of the protein produced by the abovementioned host cell transformed from the abovementioned culture medium or from the host cell.

For example, a process for the preparation of a transgenic celery as defined above, comprises the following stages:
inoculation of the celery tissues,
coculture of the celery segments and of *A. tumefaciens* bacteria,
elimination of the *A. tumefaciens* bacteria,
regeneration of the transformed celery plants (Nadel et. al., 1989).

The nucleotide sequences of the invention can be introduced into plasmids and be combined with regulation elements for expression in eukaryotic cells. These regulation elements are on the one hand transcription promoters and on the other hand transcription terminators. With the nucleotide sequences of the invention contained in the plasmids, the eukaryotic cells can be transformed with the intention of expressing a translatable mRNA which makes the synthesis of a polyol carrier in the cells possible or with the intention of expressing a non-translatable mRNA, which prevents the synthesis of a polyol carrier endogenous in the cells.

The processes of genetic modification of dicotyledons and monocotyledons are already known (Gasser et al., 1989). For expression in plants, the nucleotide sequences of the invention must be conjugated with transcription regulation elements. Such elements, called promoters, are already known (EP 375091).

In addition, coding regions with the termination signals of the transcription with which they can be correctly transcribed must be provided. Such elements are also described (Gielen et al., 1989). The initiation region of the transcription can be native and/or homologous as well as foreign and/or heterologous to the plant host. If desired, the termination regions are interchangeable amongst themselves. The DNA sequence of the initiation and termination regions of the transcription can be prepared synthetically or obtained naturally, or obtained from a mixture of natural or synthetic DNA constituents. To introduce foreign genes in higher plants, a large number of cloning vectors are available which include a replication signal for *E. coli* and a marker which allows selection of the transformed cells.

For the introduction of the nucleotide sequences of the invention into a plant host cell, in addition to transformation using *Agrobacteria*, there are many other techniques. These techniques include the fusion of protoplasts, the microinjection of DNA and electroporation, as well as ballistic methods and viral infection. Starting from the transformed plant material, whole plants can be regenerated in a suitable medium, containing antibiotics or biocides for the selection. The resulting plants can then be tested for the presence of the DNA introduced. There is no particular requirement for the plasmids regarding the injection and the electroporation. Single plasmids can be used such as the pUC derivatives. The presence of a marker gene is necessary for the regeneration of whole plants from such transformed cells. The transformed cells develop in the plants in the usual manner (McCormick et al., 1986). These plants can develop normally and be crossed with plants which possess the same transformed genes or different genes. The resulting hybrids have the corresponding phenotypic properties.

The DNA sequences of the invention can also be introduced into plasmids and be combined with regulation elements for an expression in prokaryotic cells.

The DNA sequences of the invention can also be introduced into plasmids which allow a mutagenesis or a sequence modification by means of a recombination of DNA sequences in prokaryotic or eukaryotic systems.

The transgenic plants of the invention are in particular characterized by an increase of the capacity to transport a polyol of the invention and to accumulate it in the organs from which it is extracted. They can be used to direct the flow of said polyol with the aid of said carrier towards the organs which accumulate little salt, thus facilitating extraction.

The invention also relates to a process of screening genetically modified plants with at least one nucleotide sequence of interest which comprises the following stages:
the transformation of plant cells with a vector containing an insertion sequence, said insertion sequence comprising the nucleotide sequence of interest and a nucleotide sequence coding for a polyol carrier as defined above,
the culture of the cells thus transformed on a medium containing said polyol as an only source of carbon, to obtain transgenic plants or fragments of transgenic plants containing said insertion sequence.

This process relates to plants not synthesizing polyol or plants which synthesize it.

It concerns, more particularly, the transformation of fragments or of plant cells with a nucleotide sequence coding for a polyol carrier, in particular mannitol. The screening is then carried out on a medium containing said polyol as the only source of carbon. The plants expressing the polyol carrier thus have an advantage in growth over the non-transformed plants. At this stage, it can be supposed that any plant is capable of using said polyol as a source of carbon. However, it can prove necessary to do a co-transformation with a gene coding a protein capable of degrading said polyol. The use of an active promoter only in the initial phases of regeneration or inducible by a simple compound makes it possible to restrict the expression of the polyol carrier to the selection phases.

The invention therefore concerns a simple selection system based on a plant gene which is no longer necessary once the selection is finished and on the use of a natural product as a selection agent. This system avoids having to resort to the use of products likely to be toxic, such as antibiotics.

The invention also relates to a process for obtaining transgenic plants resistant to pathogens, which comprises the following stages:
transformation of plant cells with a nucleotide sequence coding for a polyol carrier as defined above,
culture of the thus transformed cells to obtain transgenic plants or fragments of transgenic plants.

This process relates to the transformation of plants not synthesizing polyol or plants which synthesize it, with a nucleotide sequence of a polyol carrier, in particular mannitol, placed either under the control of a ubiquist promoter (type CaMV 35S) or under the control of an inducible promoter in response to the attack of the pathogen. The usefulness resides in the fact that the plant, in transporting more polyol, produced by the pathogen, towards its own cells, suppresses one of the means of defence put in place by the pathogen to fight against the activated oxygen released by the plant in response to this attack.

In order to increase the effectiveness of the process, the expression of the polyol carrier can be conjugated with an enzyme degrading said polyol.

The invention relates to a process for obtaining transgenic plants resistant to saline stress, which comprises the following stages:
transformation of plant cells with a nucleotide sequence coding for a polyol carrier as defined above, culture of the cells thus transformed to obtain transgenic plants or fragments of transgenic plants.

This process relates to the transformation of plants not synthesizing polyol or plants which synthesize it with a nucleotide sequence coding for a polyol carrier placed under the control of a phloem-specific promoter (or of the promoter of the polyol carrier). If the plant synthesizes said polyol, the increase of the transport of said polyol could lead to an accumulated tolerance to saline stress. In the opposite case, it is also advisable to introduce genes allowing the synthesis of said polyol, but limiting this synthesis to the leaves in order to avoid harmful effects on the growth of the plant.

MaDH4-YEP112A1XE: MaDH4 containing the empty plasmid;

MaDH4-AgMaT1: MaDH4 containing the plasmid with the nucleic acid of AgMaT1.

The white squares correspond to MaDH4 yeasts transformed with the empty plasmid YEP112A1XE (defined hereafter) and grown on SC-glucose medium.

The black squares correspond to MaDH4 yeasts transformed with the empty plasmid YEP 112A1XE (defined hereafter) and grown on SC-mannitol medium.

The white circles correspond to MaDH4 yeasts transformed with AgMaT1/YEP112A1XE (plasmid YEP112A1XE containing the nucleic acid of AgMaT1) and grown on SC-glucose medium.

The black circles correspond to MaDH4 yeasts transformed with AgMaT1/YEP112A1XE (plasmid YEP112A1XE containing the nucleic acid of AgMaT1) and grown on SC-mannitol medium.

The curves represent the evolution according to the absorbance time (at 600 nm) of the yeast cultures. This increase of absorbance corresponds in fact to an increase of the number of yeasts in the culture medium and is representative of the growth rate of the yeasts. Therefore the yeasts transformed with the plasmids YEP112A1XE and AgMaT1/YEP112A1XE grow on glucose but only the yeasts transformed with the AgMaT1/YEP112A1XE plasmid are capable of growing on mannitol. It is therefore proof that AgMaT1 codes for a mannitol carrier.

Figure 2:
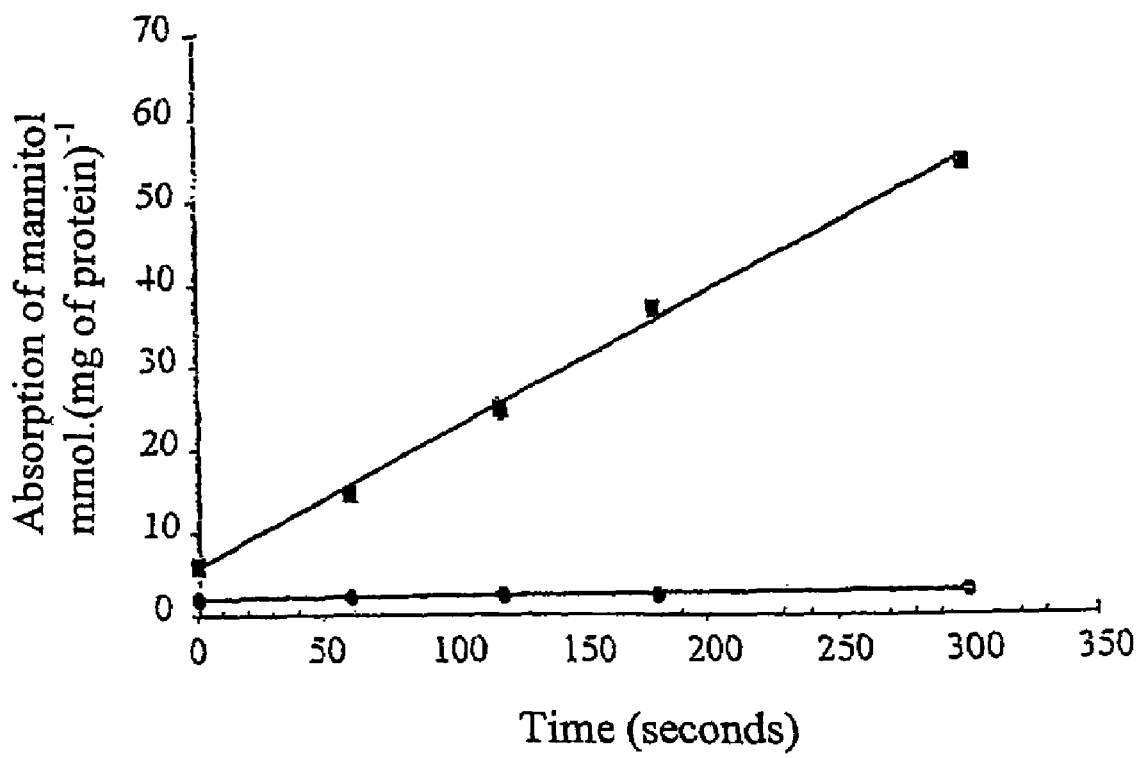

FIG. 2 represents the absorption of mannitol in cells of S. cerevisiae. The external concentration of mannitol $^3$H is 500 µM and the pH is 4.5. The squares represent the absorption in transformed cells with the nucleic acid of AgMaT1 whilst the circles represent the absorption in control cells transformed with the empty YEP112A1XE plasmid. Only the transformed cells with the AgMaT1/YEP112A1XE plasmid are capable of absorbing the mannitol $^3$H placed in the external medium.

Material and Methods

Plant Material

Celery plants (*Apium graveolens* L. dulce variety, Vert d'Elne cultivar) were grown in greenhouses according to the conditions described by Davis et al. (1988). The phloemian bundles were isolated from adult petioles according to the technique described by Daie (1987).

Bacterial Strains and Yeasts.

The following strains were used in this study: *Escherichia coli* strains DH5α (supE44, ΔlacU169 (φ80, lacZM15), hsdR17, recA, endA1, gyrA96, thi-1, relA1) (strains commercially available from Clontech). XL1Blue MRF' (Stratagene) and SOLR (Stratagene) were cultured according to standard techniques (Sambrook et al., 1989). The *Saccharomyces cerevisiae* MaDH4 strain (ura3, trp1, LEU2, gap1-1, put4-1, uga4-1), the preparation of which is indicated hereafter, expresses the mannitol dehydrogenase gene of yeast and has been used for the functional characterization of the cDNA of AgMaT1. The 2a strain was obtained by crossing between the Δα (MATα, ura3, trp1, leu2) (Marcireau et al., 1992) and Σ22574d (MATa, ura3-1, gap1-1, put4-1, uga4-1) (Jauniaux et al., 1987) strains.

Expression Vector in Yeasts

The plasmid YIP 128A1, described in Riesmeier et al. (1992) is used. The mannitol dehydrogenase gene of yeast (YEL070) was amplified by PCR (polymerization chain reaction) using the oligonucleotides MDHPST5 (5-GACTC-GAGATGACAAAATCAGACGAAACAAC-3) (SEQ ID NO: 35) and MDHBGL3 (5- GAAGATCTTCACACTTG-GTCTAAAATTTCC-3) (SEQ ID NO: 36) on the genomic DNA of the *Saccharomyces* Δα strain. The PCR product was cloned in the pBluescript SK vector digested beforehand by Pst1 and BamH1. After sequencing to confirm the sequence of the amplified gene, the PCR product was digested by Pst1 and Xba1 and cloned in the Pst1/Xba1 sites of YIP128A1. The construction was integrated into the genome of *S. cerevisiae* by the EcoV site in the leu2 gene in order to obtain the MaDH4 strain.

5' RACE-PCR (Rapid Amplification of the cDNA Ends by PCR),

The total RNA of celery leaves was isolated according to the method of Kay et al. (1987). The first cDNA strand was reverse transcribed from the total RNA with the degenerated primer (5'-CCNACNCC(G/A)AANGGNA(G/A)NA(G/A) 3) (SEQ ID NO: 37) derived from the sequence LLGFGVG (SEQ ID NO: 38) using reverse transcriptase SuperScript™ II (Stratagene). After degradation of the RNA matrix by RNaseH (Eurogentec), an anchoring primer (dC)$_{16}$ (SEQ ID NO: 39) was created at the 3' end of the single-stranded cDNA by a deoxynucleotydil transferase (GibcoBRL). A PCR amplification was carried out using the (dG)$_{16}$ (SEQ ID NO: 40) and LLGFGVG (SEQ ID NO: 38) primers under the following conditions: 2 minutes at 95° C. then 30 cycles comprising denaturation for 2 minutes at 95° C., fixation for 2 minutes at 55° C. and extension for 2 minutes at 72° C. The PCR products were analyzed by agarose gel electrophoresis then cloned in the pGEM-T Easy plasmid (Promega).

Construction and Screening of a cDNA Bank of Celery Phloem

The total RNA of the phloem bundles was isolated according to the method described by Kay et al. (1987). The polyA+ RNA was purified with the PolyATtract mRNA isolation system (Promega). A unidirectional EcOR1/XhoI bank was constructed in the Uni-ZapXR phage (Stratagene).

The recombinant phages (900,000) were screened with the radioactively labelled product of 5'RACE-PCR as probe, in accordance with the manufacturer's protocol (Stratagene). The Hybond TM-N nylon filters (Amersham) were hybridized overnight at 42° C. according to standard conditions (Stratagene). The filters were then rinsed for 15 minutes at 42° C. in SSC 2×(SSC 1×=0.15 M NaCl; 0.015 M sodium citrate) with 0.1% SDS, then for 15 minutes in the same medium but at 50° C. and 30 minutes at 50° C. in SSC 1× and 0.1% SDS. The excision in vivo was carried out on the 24 clones which produced a positive signal during the 3 successive screening turns. The identified cDNAs were partially sequenced. The sequence comparisons were carried out on the National Center for Biotechnology Information site. The transmembrane regions were predicted with the Tmpred program (Hofinann and Stoffel, 1993).

Expression of AgMaT1 in *Saccharomyces Cerevisiae*

The cDNA of AgMaT1 was ligated in the Pst1-XhoI sites of the yeast vector YEP112A1XE (Riesmeier et al., 1992). This vector allows the expression of the cDNA under the control of the yeast promoter ADH1. The MaDH4 yeast cells were rendered competent and transformed according to the protocol described by Dohmen et al. (1991).

Determination of the Growth Rate

The yeast cultures were grown on SC medium comprising either 2% glucose, or 2% mannitol. Aliquot fractions were taken regularly from the cultures and their absorbance was measured at 600 nm.

Determination of the Mannitol Dehydrogenase Activity

The cells were cultured until in logarithmic growth phase, rinsed in distilled water and resuspended at 80% (weight/volume) in extraction buffer (50 mM potassium phosphate pH 7.5, 1 mM DTT and 0.5% Triton X100). The cells were broken apart by vortex with glass beads. The cellular debris was eliminated by centrifuging and the crude extract used for the enzymatic assay. The mannitol dehydrogenase activity was measured at 30° C. according to Quain and Boulton (1987).

Measurement of the Transport of Radiolabelled Mannitol

The cells were cultured until the start of the logarithmic phase (corresponding to an absorbance of 0.6 to 600 nm), washed in distilled water and resuspended at 1% (weight/volume) in SC medium buffered to pH 4.5 with 25 mM MES. A 100 µl aliquot fraction of the cell suspension was incubated for 60, 120, 180 and 300 seconds in 100 µl of a solution containing of 500 µM [$^3$H]-mannitol. The reaction was stopped by adding 8 ml of water at 4° C. and by filtration through glass fibre filters (Sartorius). The radioactivity incorporated in the yeast cells was determined by counting using liquid scintillation (Packard). For the experiments with inhibitors or competitors, the product was added 30 seconds before the radioactive mannitol.

Study of the Expression of AgMaT1 by RT-PCR (Reverse Transcription Followed by Polymerase Chain Amplification)

The total RNA of celery phloem was isolated according to the method of Kay et al. (1987). The first strand of cDNA was reverse transcribed from the total RNA with the oligo dT primer by using the reverse transcriptase SuperScript™ II (Stratagene). After degradation of the RNA matrix by RNaseH (Eurogentec), PCR amplification was carried out using the primers 5' (ATTCTGGTGTGTTGCTCG) (SEQ ID NO: 41) and 3' (CAATGAACAGTATGATGTG) (SEQ ID NO: 42) which allow the amplification of a fragment of 661 nucleotides. The PCR conditions were as follows: 2 minutes at 95° C. then 30 cycles comprising denaturation for 30 seconds at 95° C., fixation for one minute at 47° C. and extension for 45 seconds at 72° C. The PCR products were analyzed by agarose gel electrophoresis and the intensity of the signal obtained was quantified using Photoshop 5.0 software (Adobe systems Inc.). The extension factor eIF4A (10) (Mandel et al., 1995) was used as control gene, the expression of which is invariable.

Results

Molecular Cloning of AgMaT1

A certain number of proteins which transport sugars or metabolites show similarities in their sequences. It has been suggested that these transport proteins have evolved from the duplication of an ancestral protein with 6 transmembrane regions (Maiden et al., 1987). Several preserved amino acid regions were identified such as the amino acid sequences at the ends of the $6^{th}$ and $1^{th}$ transmembrane domains, PESPR (SEQ ID NO: 43) and PETKG (SEQ ID NO: 44) respectively (Griffith et al., 1992). Comparison between the different glucose carriers (MST1, STP1, STP4, HUP1, HUP3, GLUT1), the D-xylose carrier of *L. brevis*, the arabinose carrier of *E. coli* (ARAE), the galactose carrier of *E. coli* (GALP) and the myo-inositol carriers of yeast (genes ITR1 and ITR2) indicated a preserved region LLGFGVG (SEQ ID NO: 38). This sequence was chosen as matrix for designing the degenerated 5' RACE primer for PCR.

The first strand of cDNA was reverse transcribed from the entire RNA of mature celery leaves, primed with a degenerated primer LLGFGVG (SEQ ID NO: 38). After amplification, a band of 1 kb was observed on the agarose gel. All the fragments of this PCR reaction were cloned in a pGEM-T Easy vector (Promega), and several clones were obtained.

In order to obtain an entire clone, a cDNA library was constructed originating from phloem bundles isolated from mature celery petioles and this library was screened with the 5' RACE-PCR clone. After having screened 900,000 transformants, 24 positive clones were identified. The positive transformants with inserts of approximately 1.8–2.0 kb were chosen and partially sequenced. One of these clones, called AgMaT1, was chosen for detailed analysis. It contained 1778 pb with an open reading frame which codes for a protein containing 513 amino acids with a molecular mass estimated at 56 kDa. Hydropathic analysis of the deduced sequence of amino acids indicates that AgMaT1 contains 12 transmembrane domains and a long hydrophilic central region of 77 amino acid residues. The amino acid sequence of AgMaT1 was compared with those of the databases and it was found that this sequence was related to the sugar carriers in numerous organisms. The percentage identity of the amino acids is approximately equal to 50%. However, a greater percentage of identity (65%) was found with two optional sugar carriers of *Beta vulgaris* (Beet 1 and Beet 2). An asparagine residue, which is part of an N-glycosylation consensus sequence (Asn372), is situated on the external side and therefore must be glycosylated. In addition, the consensus sequences, which are the common characteristics of the subgroup of sugar carriers of MFS, are present in AgMaT1. The sequences of PESPRXL (SEQ ID NO: 45) and PETQGRXXXE (SEQ ID NO: 46) were found respectively at the ends of the $6^{th}$ and $12^{th}$ transmembrane domains, or the (R/K)XGR(R/K) motif between the $2^{nd}$ and the $3^{rd}$ and also the $8^{th}$ and $9^{th}$ transmembrane helices (Griffith et al., 1992).

Note:

The main difficulty encountered during cloning was the total absence of characterisation of such a carrier in any living organism. In fact the only mannitol carrier is a bacteria mannitol-phospho-transferase (Boer et al., 1994) which carries out both the transport and phosphorylation of mannitol. This combined system is present in bacteria for numerous substrates but it does not exist in Eukaryotic organisms. However, according to a first strategy, a first screening of the cDNA bank was carried out with the part of the gene of mannitol-phospho-transferase corresponding to the transmembrane field. This screening did not allow a result to be obtained, which is justified a posteriori by the absence of significant homology between AgMaT1 and the mannitol-phospho-transferase.

A second strategy, which turns out not to be operational, is inspired by that used for identifying the carrier of oligosaccharides in the plants (Patent EP 0,647,273). This consists of complementing the cells of *Saccharomyces cerevisiae* with a cDNA bank in an expression vector. The yeasts are in fact capable of using mannitol as a source of carbon, but they require a fairly long induction period on mannitol. As has already been specified, no mannitol carrier has been identified in yeast. The reasoning being that if a yeast expressed a plant mannitol carrier, this would confer on it a growth advantage and that therefore, it would grow quicker on a medium containing mannitol. The operation was carried out in this way but none of the cDNAs obtained showed any of the characteristics of membrane proteins and in fact resembled transcription factors. The selection system in fact allowed the cDNA which was involved in the expression of yeast genes to be identified and not the carriers.

Faced with the above difficulties, the Inventors formulated an improbable a priori hypothesis according to which the mannitol carrier would be part of the super family of glucide carriers described by Marger and Saier (1993). To do this, a species, celery, was used in which the existence of a mannitol carrier had been demonstrated (Salmon et al., 1995) and to construct a cDNA bank from the tissue (the phloem) in which the carrier was more expressed. The second stage was the selection of the cDNA obtained according to their capacity to confer the possibility of transporting mannitol to the yeasts. In these experiments the control was the strain of yeast transformed with the empty expression plasmid. In this way the mannitol carrier function of the cDNA of AgMaT1 was demonstrated.

During this experiment, other sequences were identified: in total 24 clones were obtained. Among all these clones, two were sequenced which showed the hydropathy profiles of carriers. The first, M22 (AgMaT1), conferred the ability to transport mannitol to the yeasts whilst the second, M7, did not confer it.

Construction of a Strain of Yeast Capable of Metabolizing Intracellular Mannitol Initial studies were carried out in order to characterize the ability of a yeast to absorb and to metabolize mannitol (Quain and Boulton, 1987). Out of the 40 polyploid strains of *S. cerevisiae* screened, half of them have shown good growth on 5% mannitol after long-term adaptation (Quain and Boulton, 1987). As a result, it was decided to test 50 different strains of yeasts for their ability to transport and metabolize the mannitol and 2 strains were retained. This was firstly carried out by analyzing the growth characteristics on a medium containing mannitol as the only carbon source. Σ22574d, generally deficient in a general carrier of amino acids and carrier of proline, is incapable of growth on a medium containing mannitol as the only carbon source. On the contrary, Δα was capable of growing on mannitol after long-term adaptation. After adaptation, the strain could be maintained successfully on a solid medium containing 5% mannitol. But maintenance of the adapted Δα strain on a solid medium only containing glucose leads to the total loss of the adapted growth. Such a growth adaptation on mannitol is probably due to the induction of the key degradation enzymes or the transport permeases. In accordance with the previous observations, NAD$^+$ dependant D-mannitol dehydrogenase could be detected in the Δα yeasts (Table 1).

TABLE 1

Activity of mannitol dehydrogenase in different yeast strains. The strains are developed in a liquid medium containing either 2% glucose or 2% mannitol. The results are the averages ± SD of the three independent experiments. ND, not detected.

| | Activity (μmol of oxidized mannitol · (mg of protein)$^{-1}$ · min$^{-1}$) | |
|---|---|---|
| Strain | glucose | mannitol |
| Δα | 0.011 ± 0.003 | 0.240 ± 0.007 |
| Σ22574d | 0.006 ± 0.002 | ND |
| 2a | 0.001 ± 0.001 | ND |
| MaDH4 | 0.410 ± 0.011 | ND |

In order to obtain an auxotrophy to tryptophan, the Δα strain (Trp$^-$) was crossed with the Σ22574d strain (Trp$^+$). Yeast 2a was chosen, which cannot grow on a medium containing mannitol, with an auxotrophy to tryptophan and to leucine. No mannitol dehydrogenase activity was detected in cells 2a (Table 1). It was necessary to introduce a limited mannitol hydrolysis activity inside the yeast. The cDNA of the gene of the yeast mannitol dehydrogenase was cloned in YIP128A1 under the control of the ADH1 promoter and it was integrated in a stable manner in the leu2 gene of 2a. Several transformants have shown a mannitol dehydrogenase activity. The strain with the most significant activity, called MaDH4, was used for the subsequent analyses (Table 1).

Heterologous Expression of the AgMaT1 Protein

For a subsequent characterization of the function of the AgMaT1 protein, it was necessary to express the carrier in a functional manner in a heterologous system such as yeast cells. The cDNA of AgMaT1 was sub-cloned in the PstI/XhoI sites of the YEP 112A1XE shuttle vector which has a promoter/terminator box of the gene of alcohol dehydrogenase ADH1 of *S. cerevisiae* (Riesmeier et al., 1992). The competent MaDH4 cells were transformed with this construction and YEP 112A1XE was used as control.

Figure 1:
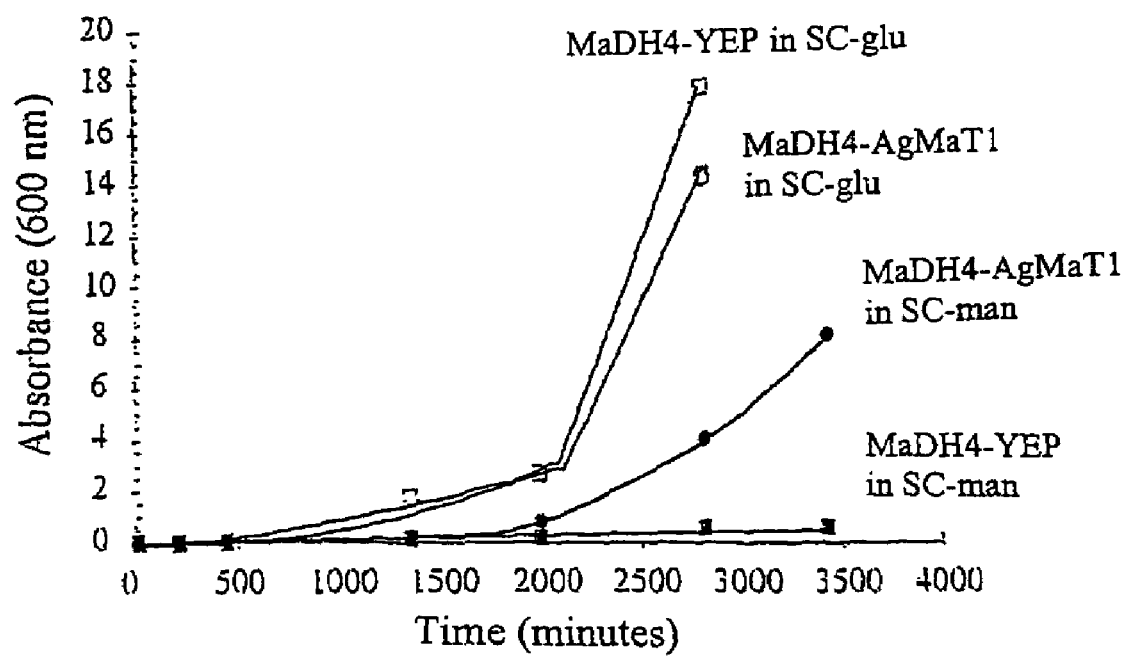
FIG. 1 represents the growth test of the yeast MaDH4 expressing the proteic sequence AgMaT1. The cDNA of AgMaT1, under the control of the promoter ADH1, was introduced in the cells of the MaDH4 strain, and the growth of the transformed cells on mannitol was studied. The transformed cells were grown on the SC (synthetic complete) liquid medium without tryptophan containing either 2% glucose (SC-glu) or 2% mannitol (SC-mann).

All of the constructions were firstly tested for their ability to grow on mannitol as the only carbon source. As indicated in FIG. 1, the MaDH4 strain, transformed with the empty plasmid YEP 112A1XE is not capable of growing on mannitol. The cells expressing AgMaT1 could grow very well on this polyol. In order to directly test the ability of the transformed cells to transport mannitol, the yeast cells were incubated in a medium containing [$^3$H]-mannitol for a few seconds to several minutes, the cells were washed and the radioactivity absorbed was measured by electric scintillation counting. FIG. 2 indicates that the transport of mannitol in the control cells of *S. cerevisiae* is negligible. However, the MaDH4 yeast strains, expressing AgMaT1, transport the [$^3$H]-mannitol at high speeds when they grow on a medium containing mannitol. The same result is obtained with the cells of transformed yeast growing on glycerol (data not indicated).

Other polyols such as dulcitol, sorbitol, xylitol, myo-inositol appear capable of inhibiting by half the absorption of mannitol. The oside form of mannitol, mannose, appears to be recognized by AgMaT1.

Variation of the Expression of AgMaT1 During Saline Stress

The expression of AgMaT1 was monitored in plants having been subjected to saline stress for 4 weeks (daily watering with 300 mM of NaCl, Noiraud et al., 2000). The phloem of these plants as well as of the corresponding control plants (watered with water not containing NaCl) was removed in order to extract the RNA which was used to carry out RT-PCR reactions. If the expression of AgMaT1 in the phloem of the control plants is taken as base 100, the expression of AgMaT1 in the phloem of plants treated with NaCl is 500%, which represents a very significant stimulation and is in accordance with the role of AgMaT1 in saline stress tolerance in celery.

Transformation Protocol of Petioles or Leaves of Celery

Celery plants (approximately 10 cm in height) regenerated from embryogenic cells are used as plant material for the transformation.

Inoculation of the Celery Tissues

*Agrobacterium tumefaciens* bacteria are cultured for 24 hours at 28° C. under agitation in LB medium (Liquid Broth: 1% tryptone, 0.5% autolytic extract of yeast, 0.5% NaCl) with the appropriate antibiotic.

The petioles of celery plants are fragmented into sections of approximately 0.5 cm. For each fragment, a longitudinal section is produced. The celery segments are incubated in MS medium (Murashige & Skoog) 1× (normal concentration, i.e. no dilution) liquid containing $1/25^{th}$ of the culture of *Agrobacterium tumefaciens* bacteria for 60 minutes at ambient temperature.

Composition of the MS Medium

| Macro-elements | |
|---|---|
| $CaCl_2$ | 2.99 mM |
| $KH_2PO_4$ | 1.25 mM |
| $KNO_3$ | 18.79 mM |
| $MgSO_4$ | 1.50 mM |
| $NH_4NO_3$ | 20.61 mM |

| Vitamins | |
|---|---|
| Glycine | 26.64 mM |
| Myo-inositol | 0.56 mM |
| Nicotinic acid | 4.06 µM |
| Pyridoxine-HCl | 2.43 µM |
| Thiamine-HCl | 0.30 µM |

| Micro-elements | |
|---|---|
| $CoCl_2$, 6 $H_2O$ | 0.11 µM |
| $CuSO_4$, 5 $H_2O$ | 0.10 µM |
| FeNaEDTA | 0.10 µM |
| $H_3Bo_3$ | 0.10 µM |
| KI | 5.00 µM |
| $MnSO_4$, $H_2O$ | 0.10 mM |
| $Na_2MoO_4$, 2 $H_2O$ | 1.03 µM |
| $ZnSO_4$, 7 $H_2O$ | 29.91 µM |

The excess bacteria are then removed from the celery segments by arranging them on absorbent paper for 2–3 minutes.

Coculture of the Celery Segments and the *A. Tumefaciens* Bacteria

The cambial surface of the celery segments is left in contact with the gelosed regeneration medium RM. The Petri dishes are placed in a chamber air-conditioned at 25° C. for 48 hours and subjected to light/dark cycles of 16 hours/8 hours.

Elimination of the *A. Tumefaciens* Bacteria

After coculture for 48 hours, the celery segments are removed form the dishes of RM medium and transferred into MS 1 × liquid supplemented with cefotaxime at a final concentration of 250 µg/mL. After incubation for 60 minutes, the celery segments are dried on absorbent paper for 2–3 minutes.

Regeneration of Transformed Celery Plants

The cambial surface of the celery segments is left in contact with a gelosed callogenesis initiation medium CIM. The CIM Petri dishes are placed in a chamber air-conditioned at 25° C. and subjected to light/dark cycles of 16 hours/8 hours until the development of calluses (2–3 weeks). The celery segments are then transferred onto a gelosed organogenesis induction medium OIM (2–3 weeks). After the appearance of buds, these are removed and placed on gelosed rooting medium RM. A few weeks (3–4 weeks) are necessary for the development of young celery shoots.

Composition of the Media

Regeneration Medium RM

| | |
|---|---|
| MS | 1× |
| Mannitol | 3.0% |
| Saccharose | 1.5% |
| Casein hydrolysate | 100.0 mg/L |
| 6-Benzylaminopurine (BAP) | 1.0 mg/L |
| α-naphthylacetic acid (NAA) | 0.1 mg/L |
| Gibberellic acid ($GA_3$) | 0.1 mg/L |
| Agar | 0.8% |

Callogenesis Initiation Medium (CIM)

| | |
|---|---|
| MS | 1× |
| Mannitol | 3.0% |
| Saccharose | 1.5% |
| Casein hydrolysate | 100.0 mg/L |
| 6-Benzylaminopurine (BAP) | 1.0 mg/L |
| α-naphthylacetic acid (NAA) | 0.1 mg/L |
| Gibberellic acid ($GA_3$) | 0.1 mg/L |
| Kanamycin | 125.0 mg/L |
| Cefotaxime | 200.0 mg/L |
| Agar | 0.8% |

Organogenesis Induction Medium (OIM)

| | |
|---|---|
| MS | 1× |
| Mannitol | 3.0% |
| Saccharose | 1.5% |
| Casein hydrolysate | 100.0 mg/L |
| 6-Benzylaminopurine (BAP) | 1.0 mg/L |
| Gibberellic acid ($GA_3$) | 0.1 mg/L |
| Kanamycin | 75.0 mg/L |
| Cefotaxime | 200.0 mg/L |
| Agar | 0.8% |

Rooting Medium (RM)

| | |
|---|---|
| MS | 1× |
| Mannitol | 3.0% |
| Saccharose | 1.5% |
| Casein hydrolysate | 100.0 mg/L |
| α-indolyacetic acid (IAA) | 0.1 mg/L |
| Kanamycin | 75.0 mg/L |
| Cefotaxime | 200.0 mg/L |
| Agar | 0.8% |

REFERENCES

Lewis D H (1984) Physiology and metabolism of alditols. In D H Lewis eds, Storage carbohydrates in vascular plants, Cambridge University Press, Cambridge, pp 157–179, Boer et al. (1994) *Journal of Biological Chemistry*, 269: 17863–17871, Daie J (1987) Sucrose uptake in isolated phloem of celery is a single saturable transport system. *Planta* 171: 474–482, Davis et al. (1988) Biosynthesis of sucrose and mannitol as a function of leaf age in celery (*Apium graveolens* L.). *Plant Physiol.* 86: 129–133, Dohmen et al. (1991) An efficient transformation procedure enabling long term storage of competent cells of various yeast genera. *Yeast* 7: 691–692, Gasser et al. (1989) *Science*, 244: 1293–1299, Gielen et al. (1989) *EMBO J*, 8: 23–29, Griffith et al. (1992) Membrane transport proteins: implications of sequence comparisons. *Curr. Opin. Cell Biol.* 4: 684–695, Hofmann K and Stoffel W (1993) Tmbase—A database of membrane spanning protein segments. Biol. Chem. Hoppe-Seyler 347: 166, Jauniaux et al. (1987) Nitrogen catabolite regulation of proline permease in *Saccharomyces cerevisiae*. Cloning of the PUT4 gene and study of PUT4 RNA levels in the wild-type and the mutant strains. *Eur. J. Biochem.* 164: 601–606, Kay et al. (1987) Duplication of CaMV $^{35}$S promoter sequences creates a strong enhancer for plant genes. *Sci.* 236: 1299–1302, Maiden et al. (1987) Mammalian and bacterial sugar porters are homologous. *Nature* 325: 641–643, Mandel et al. (1995) *Plant Mol. Biol.*, 29: 995–1004, Marcireau et al. (1992) Construction and growth properties of a yeast strain defective in sterol 14-reductase. *Curr Genet*, 22: 267–272, Marger M D, Saier J M H (1993) A major superfamily of transmembrane facilitators that catalyse uniport, symport and antiport. *Trends Biochem. Sci.* 18: 13–20, McCormick et al. (1986) *Plant Cell Reports*, 5: 81–84, Nadel et al. (1989) *Plant Cell and Organ Culture*, 18: 181–189, Noiraud et al. (2000) The sucrose transporter of celery. Identification and expression during salt stress. *Plant Physiology*, 122: 1447–1455, Quain D E, Boulton C A (1987) Growth and metabolism of mannitol by strains of *Saccharomyces cerevisiae*. *J. Gen. Bacteriol.* 133: 1675–1684, Riesmeier et al. (1992) Isolation and characterization of a sucrose carrier cDNA from spinach by functional expression in yeast. *EMBO J.* 11: 4705–4713, Salmon et al. (1995) Study of sucrose and mannitol transport in plasma-membrane vesicles from phloem and non-phloem tissues of celery (*Apium graveolens* L.) petioles. *Planta* 197: 76–83, Sambrook et al. (1989) Molecular cloning. Cold Spring Harbor Laboratory Press.

The invention claimed is:

1. A protein, comprising:
   sequence SEQ ID NO: 2.
2. An isolated polypeptide according to claim 1, wherein said polypeptide consists of SEQ ID NO: 2.

* * * * *

SEQUENCE LISTING

```
<160> NUMBER OF SEQ ID NOS: 46

<210> SEQ ID NO 1
<211> LENGTH: 1766
<212> TYPE: DNA
<213> ORGANISM: Apium graveolens
<220> FEATURE:
<221> NAME/KEY: CDS
<222> LOCATION: (17)..(1555)

<400> SEQUENCE: 1
ggcacgagga gcttct atg att acc ggc gaa gtt tcc gtc gat tca tat gat        52
               Met Ile Thr Gly Glu Val Ser Val Asp Ser Tyr Asp
                 1               5                  10 act aac aag cct aaa cct aaa agg aat aag tat gct ttt gct tgt gct       100
Thr Asn Lys Pro Lys Pro Lys Arg Asn Lys Tyr Ala Phe Ala Cys Ala
         15                  20                  25 ctt tta gct tcc atg aat tcc atc tta ctc ggc tat gac acc gga gtg       148
Leu Leu Ala Ser Met Asn Ser Ile Leu Leu Gly Tyr Asp Thr Gly Val
     30                  35                  40 ttg agt gga gca tca ata tac ata aag gaa gat ctc cat ttc tcc gac       196
Leu Ser Gly Ala Ser Ile Tyr Ile Lys Glu Asp Leu His Phe Ser Asp
 45                  50                  55                  60 gtt caa atc gaa ata atc atc gga atc atc aac atc tac tct ctt ctt       244
Val Gln Ile Glu Ile Ile Ile Gly Ile Ile Asn Ile Tyr Ser Leu Leu
```

|     |     |     |     |     |     |     |     |     |     |     |     |      |
| --- | --- | --- | --- | --- | --- | --- | --- | --- | --- | --- | --- | ---- |
| ggt | tcg | gcc | ata | gcc | gga | agg | acc | tcg | gac | tgg | ata | ggc | aga | cgt | tac | 292 |
| Gly | Ser | Ala | Ile | Ala | Gly | Arg | Thr | Ser | Asp | Trp | Ile | Gly | Arg | Arg | Tyr |
|     |     |     | 80  |     |     |     |     | 85  |     |     |     |     | 90  |     |     | acc atg gta cta gct ggt atc ata ttt ttt cta gga gcc att ttc atg     340
Thr Met Val Leu Ala Gly Ile Ile Phe Phe Leu Gly Ala Ile Phe Met
            95                  100                 105 ggg ctt gct aca aac ttt gcc ttt ctc atg ttt ggt cgc ttt gtt gct     388
Gly Leu Ala Thr Asn Phe Ala Phe Leu Met Phe Gly Arg Phe Val Ala
        110                 115                 120 gga att ggt gtc ggt tat gcc atg atg atc gct ccc gtc tac act gcc     436
Gly Ile Gly Val Gly Tyr Ala Met Met Ile Ala Pro Val Tyr Thr Ala
125                 130                 135                 140 gag gtt gct ccg tcg tct tcc cgt ggt ttc ctc act tct ttt cct gag     484
Glu Val Ala Pro Ser Ser Ser Arg Gly Phe Leu Thr Ser Phe Pro Glu
                145                 150                 155 gtt ttc att aat tct ggt gtg ttg ctc ggg tat gta tcc aac ttt gca     532
Val Phe Ile Asn Ser Gly Val Leu Leu Gly Tyr Val Ser Asn Phe Ala
            160                 165                 170 ttt gcc aag tgc cca ctt tgg tta ggc tgg aga att atg ctg gga att     580
Phe Ala Lys Cys Pro Leu Trp Leu Gly Trp Arg Ile Met Leu Gly Ile
        175                 180                 185 gga gca ttt cct tca gtt gcc ttg gcc ata att gtg tta tat atg cca     628
Gly Ala Phe Pro Ser Val Ala Leu Ala Ile Ile Val Leu Tyr Met Pro
190                 195                 200 gag tcc cca cgt tgg ctc gtt atg cag ggt cga ctt ggt gaa gcg agg     676
Glu Ser Pro Arg Trp Leu Val Met Gln Gly Arg Leu Gly Glu Ala Arg
205                 210                 215                 220 act gta ctt gag aaa act tct act tcc aaa gaa gaa gct cac caa aga     724
Thr Val Leu Glu Lys Thr Ser Thr Ser Lys Glu Glu Ala His Gln Arg
                225                 230                 235 ctg tct gat att aag gaa gct gct ggg att gat aaa gat tgt aat gac     772
Leu Ser Asp Ile Lys Glu Ala Ala Gly Ile Asp Lys Asp Cys Asn Asp
            240                 245                 250 gat gtt gtt caa gtt cca aaa cgt acc aaa gac gaa gca gtg tgg aaa     820
Asp Val Val Gln Val Pro Lys Arg Thr Lys Asp Glu Ala Val Trp Lys
        255                 260                 265 gaa ttg att ctt cac cct aca aaa cct gtt cgc cac gct gca att acg     868
Glu Leu Ile Leu His Pro Thr Lys Pro Val Arg His Ala Ala Ile Thr
270                 275                 280 ggt att ggt att cat ttc ttc caa cag gct tgt ggt att gat gct gtt     916
Gly Ile Gly Ile His Phe Phe Gln Gln Ala Cys Gly Ile Asp Ala Val
285                 290                 295                 300 gtt tta tac agc cct cga att ttt gaa aaa gct ggt atc aaa agt aat     964
Val Leu Tyr Ser Pro Arg Ile Phe Glu Lys Ala Gly Ile Lys Ser Asn
                305                 310                 315 agt aaa aag ctc ctt gcg aca att gct gtt gga gtc tgc aaa aca gtc     1012
Ser Lys Lys Leu Leu Ala Thr Ile Ala Val Gly Val Cys Lys Thr Val
            320                 325                 330 ttt att ctg ata tca acg ttt cag ctg gac aaa att gga cga cgc ccc     1060
Phe Ile Leu Ile Ser Thr Phe Gln Leu Asp Lys Ile Gly Arg Arg Pro
        335                 340                 345 ctg atg cta aca agt atg ggg ggt atg gtt att gct cta ttt gta ctg     1108
Leu Met Leu Thr Ser Met Gly Gly Met Val Ile Ala Leu Phe Val Leu
350                 355                 360 gca ggc tca ttg acg gtt att aac aaa tca cat cat act ggt cat tgg     1156
Ala Gly Ser Leu Thr Val Ile Asn Lys Ser His His Thr Gly His Trp
365                 370                 375                 380 gct ggt ggt ttg gca ata ttt aca gtg tat gct ttt gtg tcg ata ttt     1204

-continued

```
Ala Gly Gly Leu Ala Ile Phe Thr Val Tyr Ala Phe Val Ser Ile Phe
            385                 390                 395 tca agt ggc atg ggt cca att gct tgg gtc tat agc tcc gag gtg ttc    1252
Ser Ser Gly Met Gly Pro Ile Ala Trp Val Tyr Ser Ser Glu Val Phe
            400                 405                 410 cct ttg agg cta aga gct caa ggt tgt agt atc gga gtg gca gtt aac    1300
Pro Leu Arg Leu Arg Ala Gln Gly Cys Ser Ile Gly Val Ala Val Asn
        415                 420                 425 cgt ggc atg agt ggc ata att gga atg aca ttt ata tcg atg tac aaa    1348
Arg Gly Met Ser Gly Ile Ile Gly Met Thr Phe Ile Ser Met Tyr Lys
    430                 435                 440 gcc atg act att ggt ggt gca ttc ctt tta ttt gct gtg gtt gca tct    1396
Ala Met Thr Ile Gly Gly Ala Phe Leu Leu Phe Ala Val Val Ala Ser
445                 450                 455                 460 atc gga tgg gtc ttt atg tac aca atg ttc ccc gag aca caa ggt aga    1444
Ile Gly Trp Val Phe Met Tyr Thr Met Phe Pro Glu Thr Gln Gly Arg
                465                 470                 475 aat ctc gaa gaa att gag tta ttg ttt ggc agc tac ttt ggc tgg agg    1492
Asn Leu Glu Glu Ile Glu Leu Leu Phe Gly Ser Tyr Phe Gly Trp Arg
            480                 485                 490 aag aca ttg aag gat ttg aag gca aaa gaa gct gct gaa gca aag agt    1540
Lys Thr Leu Lys Asp Leu Lys Ala Lys Glu Ala Ala Glu Ala Lys Ser
        495                 500                 505 cgc gag agt gaa gtt tagcagtcag atgaattag ggttcaaaga tgttatatta    1595
Arg Glu Ser Glu Val
        510 gctctgtgta gagggtagtt ttagagaagc ccttagtatg tgttggagta tgtgtgatta   1655 ttaaccatca cccgataatt tagaataagg gtgtcaaaga acaattaccc atttcttatg   1715 tggtaatcta ttgaaaagaa tttgcccaat ggtaaaaaaa aaaaaaaaaa a            1766
```

<210> SEQ ID NO 2
<211> LENGTH: 513
<212> TYPE: PRT
<213> ORGANISM: Apium graveolens

<400> SEQUENCE: 2

```
Met Ile Thr Gly Glu Val Ser Val Asp Ser Tyr Asp Thr Asn Lys Pro
 1               5                  10                  15

Lys Pro Lys Arg Asn Lys Tyr Ala Phe Ala Cys Ala Leu Leu Ala Ser
            20                  25                  30

Met Asn Ser Ile Leu Leu Gly Tyr Asp Thr Gly Val Leu Ser Gly Ala
        35                  40                  45

Ser Ile Tyr Ile Lys Glu Asp Leu His Phe Ser Asp Val Gln Ile Glu
    50                  55                  60

Ile Ile Ile Gly Ile Ile Asn Ile Tyr Ser Leu Leu Gly Ser Ala Ile
65                  70                  75                  80

Ala Gly Arg Thr Ser Asp Trp Ile Gly Arg Arg Tyr Thr Met Val Leu
                85                  90                  95

Ala Gly Ile Ile Phe Phe Leu Gly Ala Ile Phe Met Gly Leu Ala Thr
            100                 105                 110

Asn Phe Ala Phe Leu Met Phe Gly Arg Phe Val Ala Gly Ile Gly Val
        115                 120                 125

Gly Tyr Ala Met Met Ile Ala Pro Val Tyr Thr Ala Glu Val Ala Pro
    130                 135                 140

Ser Ser Ser Arg Gly Phe Leu Thr Ser Phe Pro Glu Val Phe Ile Asn
145                 150                 155                 160
```

Ser Gly Val Leu Leu Gly Tyr Val Ser Asn Phe Ala Phe Ala Lys Cys
                165                 170                 175

Pro Leu Trp Leu Gly Trp Arg Ile Met Leu Gly Ile Gly Ala Phe Pro
            180                 185                 190

Ser Val Ala Leu Ala Ile Ile Val Leu Tyr Met Pro Glu Ser Pro Arg
        195                 200                 205

Trp Leu Val Met Gln Gly Arg Leu Gly Glu Ala Arg Thr Val Leu Glu
    210                 215                 220

Lys Thr Ser Thr Ser Lys Glu Glu Ala His Gln Arg Leu Ser Asp Ile
225                 230                 235                 240

Lys Glu Ala Ala Gly Ile Asp Lys Asp Cys Asn Asp Asp Val Val Gln
                245                 250                 255

Val Pro Lys Arg Thr Lys Asp Glu Ala Val Trp Lys Glu Leu Ile Leu
            260                 265                 270

His Pro Thr Lys Pro Val Arg His Ala Ala Ile Thr Gly Ile Gly Ile
        275                 280                 285

His Phe Phe Gln Gln Ala Cys Gly Ile Asp Ala Val Val Leu Tyr Ser
    290                 295                 300

Pro Arg Ile Phe Glu Lys Ala Gly Ile Lys Ser Asn Ser Lys Lys Leu
305                 310                 315                 320

Leu Ala Thr Ile Ala Val Gly Val Cys Lys Thr Val Phe Ile Leu Ile
                325                 330                 335

Ser Thr Phe Gln Leu Asp Lys Ile Gly Arg Arg Pro Leu Met Leu Thr
            340                 345                 350

Ser Met Gly Gly Met Val Ile Ala Leu Phe Val Leu Ala Gly Ser Leu
        355                 360                 365

Thr Val Ile Asn Lys Ser His His Thr Gly His Trp Ala Gly Gly Leu
    370                 375                 380

Ala Ile Phe Thr Val Tyr Ala Phe Val Ser Ile Phe Ser Ser Gly Met
385                 390                 395                 400

Gly Pro Ile Ala Trp Val Tyr Ser Ser Glu Val Phe Pro Leu Arg Leu
                405                 410                 415

Arg Ala Gln Gly Cys Ser Ile Gly Val Ala Val Asn Arg Gly Met Ser
            420                 425                 430

Gly Ile Ile Gly Met Thr Phe Ile Ser Met Tyr Lys Ala Met Thr Ile
        435                 440                 445

Gly Gly Ala Phe Leu Leu Phe Ala Val Val Ala Ser Ile Gly Trp Val
    450                 455                 460

Phe Met Tyr Thr Met Phe Pro Glu Thr Gln Gly Arg Asn Leu Glu Glu
465                 470                 475                 480

Ile Glu Leu Leu Phe Gly Ser Tyr Phe Gly Trp Arg Lys Thr Leu Lys
                485                 490                 495

Asp Leu Lys Ala Lys Glu Ala Ala Glu Ala Lys Ser Arg Glu Ser Glu
            500                 505                 510

Val

<210> SEQ ID NO 3
<211> LENGTH: 2056
<212> TYPE: DNA
<213> ORGANISM: Beta vulgaris

<400> SEQUENCE: 3
atcaatccaa aaaatcaaa aggaaacaaa ttcccatctt tccttacttt ctctctcttt    60
ttctctctct tattggtgag aaataagtga gccatgagtg aaggaactaa taaagccatg   120

```
tcagacccac caccaacaac tgcaagcaaa gtaatagcag attttgatcc tttaaagaag    180
cctcctaaga gaaacaagtt tgcttttgct tgtgctactt tggcttctat gacttctgtt    240
ttacttggtt atgacattgg agtaatgagt ggtgcaataa tctacctcaa agaagactgg    300
cacattagtg acacacaaat aggagttcta gtcggaatct aaacatcta ctgcctcttc     360 ggctctttcg cagctggtcg aacttccgat tggatcggac gacgttacac catcgtatta    420
gctggtgcaa tcttcttcgt tggcgcacta ctcatgggtt tcgccacaaa ctacgcattt    480
ctcatggtag gccgttttgt aacaggaata ggtgttggtt atgcacttat gatcgcacct    540
gtttacactg cagaggtttc tcctgcttct tcaagaggat ttcttacctc ttttcctgag    600
gttttcatca atgcaggaat tttgcttgga tatatatcta accttgcatt ttcaagcctc    660
ccaactcatt tgagctggag gtttatgctc ggaatcgggg cgattccgag catattttg     720 gctattggag tgcttgctat gcctgagtca ccgcggtggc ttgttatgca gggaaggctt    780
ggagatgcta agaaggtgct taatcgcata tctgactcgc ctgaggaggc tcaacttagg    840
ctcagtgaga ttaagcagac agcaggaatc ccagctgagt gtgatgaaga catctataag    900
gttgaaaaaa caaagataaa atcagggaat gcagtttgga aagagctctt cttcaaccct    960
actcccgcag tgaggcgtgc agtgattgca ggtatcggaa ttcactttt ccagcaagct    1020 tccggcatcg acgccgtggt tttatacagt ccaaggatct ttcagagtgc tggaatcaca   1080
aatgcacgta acagttact tgcaacagta gctgtaggag ttgttaagac acttttcata    1140
ttagttgcta catttcaatt agacaagtat ggtagaaggc ctttactatt aacaagtgtt    1200
ggtggtatga tcatagccat cttaacctta gccatgtctt taactgttat tgatcactct   1260
catcacaaga ttacatggc tatagccttg tgtataacca tggtttgtgc tgtcgttgcg    1320
tcgttttcga ttggtttagg accaattaca tgggtatata gttcagaggt tttcccctta    1380
aggttaaggg ctcaaggtac tagcatgggt gtggctgtta atagagttgt aagtggtgtt    1440
atttcaatat ttttcttgcc tttgtcacat aagattacaa caggtggtgc cttcttttg    1500 ttcggaggga ttgctattat tgcttggttc ttcttcttga cgtttcttcc tgagactaga    1560
gggcgtacac ttgagaatat gcatgagttg tttgaagatt ttagatggag ggagtcattt    1620
ccaggcaaca agtcaaataa tgatgagaat agcacaagaa aacaaagtaa tggtaatgac    1680
aagagtcaag tacaattggg agaaactact actagtagtg tacaagtata gttatgtacg    1740
gatgttatgt catgtatagc tgttcgactt ttaatgacga taattaatct caaatcgaac    1800
aagtttctaa gatgtgtgtg tataagatgt gcgtgatgta cgtacttgtt atacacatgt    1860
tgttcttaga atgtgatcct ctttattttc gcaaatacat tgtagcaaat taaagtaatc    1920
taattatagg ataccaaatg gttcaaaaaa caatgtcttt tgtgtgattt tgtatgatgc    1980
ttcatcattt gtcagtttac ccttttttg gtaatgaaga caaataaat tcatgagttt     2040 agctttaaaa aaaagr                                                    2056

<210> SEQ ID NO 4
<211> LENGTH: 1925
<212> TYPE: DNA
<213> ORGANISM: Beta vulgaris

<400> SEQUENCE: 4 ctcttttct ctctcttatt ggtgagaaat aagtgagcca tgagtgaagg aactaataaa    60
gccatgtcag acccaccacc aacaactgca agcaaagtaa tagcagattt tgatccttta   120
```

-continued

```
aagaagcctc ctaagagaaa caagtttgct tttgcttgtg ctactttggc ttctatgact      180
tctgttttac ttggttatga cattggagta atgagtggtg caataatcta cctcaaagaa      240
gactggcaca ttagtgacac acaaatagga gttctagtcg gaatcttaaa catctactgc      300
ctcttcggct ctttcgcagc tggtagaaca tccgattgga tcggacgacg ttacactatc      360
gtgttagctg gtgcaatctt cttcgttggc gcactactca tgggtttcgc cacaaactac      420
gcatttctta tggtaggccg ttttgtaaca ggaataggtg ttggttatgc acttatgatc      480
gcacctgttt acactgcaga ggtttctcct gcttcttcaa gaggatttct tacctctttt      540
cctgaggttt tcatcaatgc aggaattttg cttggatata tatctaatct cgcattttca      600
agcctcccaa ctcatttgag ctggaggttt atgctcggaa tcgggcgat tccgagcata       660
ttttggcta ttggagtgct tgctatgcct gagtcaccga ggtggcttgt tatgcaggga       720
aggcttggag atgctaagaa ggtgcttaat cgaatatctg actcgcctga ggaggctcaa      780
cttaggctca gtgagattaa gcagacagca ggaatcccag ctgagtgtga tgaagacata      840
tataaggttg aaaaaacaaa gataaaatca gggaatgcag tttggaaaga gctcttcttc      900
aaccctactc ccgcagtgag gcgtgcagtg attgcaggta tcggaattca cttttttccag     960
caagcttccg gcatcgacgc cgtggtttta tacagtccaa ggatctttca gagtgctgga     1020
atcacaaatg cacgtaaaca gttacttgca acagtagctg taggagttgt taagacactt     1080
ttcatattag ttgctacatt tcaattagac aagtatggta gaaggccttt actattaaca     1140
agtgttggtg gtatgatcat agccatctta accttagcca tgtctttaac tgttattgat     1200
cactctcatc acaagattac atgggctata gccttgtgta taaccatggt ttgtgctgtc     1260
gttgcgtcgt tttcgattgg tttaggacca attacatggg tatatagttc agaggttttc     1320
cccttgaggt taagggctca aggtactagc atgggtgtgg ctgttaatag agttgtaagt     1380
ggtgttattt caatattttt cttgcctttg tcacataaga ttacaacagg tggtgccttc     1440
tttttgttcg gagggattgc tattattgct tggttcttct tcttgacgtt tcttcctgag     1500
actagagggc gtacacttga gaatatgcat gagttgtttg aagatttttag atggagggag    1560
tcatttccag gcaacaagtc aaataatgat gagaatagta caagaaaaca aagcaatggt     1620
aatgacaaga gtcaagtaca attgggagaa actactacta gtactactgt tacaaatgac     1680
aatcactgag aaacaattgt tagtgtacaa gtatagttat gtacggatgt tatgtcatgt     1740
atagctgttc gacttttaat gataattaat cttaagtcga acaagcttct aagatgtgtg     1800
tgtataacat ggcgtgatgt acgcgcttgt tatacacatg ttgttcttag aatgtgatcc     1860
tctttatttt cgcaaataca ttgtagcaaa ttaaagtaat ctaattatag gataccaaat     1920
ggaaa                                                                 1925
```

<210> SEQ ID NO 5
<211> LENGTH: 1715
<212> TYPE: DNA
<213> ORGANISM: Arabidopsis thaliana

<400> SEQUENCE: 5

```
tcattgtcca tccacaactt cattgtcttt gctcatagaa ttattcttct tgtttgcggt       60
gtagctcccg aagagagtct ccatctcctc tagaggtata ccacgtgtct ccgggaggaa      120
agtgaagaag aagacccatg cggcggcagc aactccggcg aatagaagga acgcaccgcc      180
gatggtgaga ccttttagaaa gagataggaa tgtcattcca ataataccac tcattagtct     240
attcaacatc actcctaaac ttgccccttg agctcttagc ctcacaggga atatctctga     300
```

-continued

```
gcagtagacc cacgtcacgg ggcctgcacc tattgagaat gttgccacaa aagtcatcac      360
cgtcgtaacg gcgagcccta tagcccactt gagtgtttgc ccggggttcc tgttgatcac      420
cgtgagacta gttccaagtg cggtcaagga agaaacatt ccgcccatac tcgtaagcaa       480
caaggcacga cgtccgaacc gatccaccac acaagtccct accacgatga agagagtctt      540
gacaactccg acagcgaccg tagccaagag ctggtcattc ttggacttca gtccagcctt      600
tgagaagatt gtcggagagt aaagcacaac cgcatcaatt ccagaggctt gctgggcgaa      660
atgaatacca aggcatgcta tgaggatgtg tcgaacggac ggggttggtc gaacgagaag      720
gtccttccac acgccttttc cagcgctctt tttattcgga acgactataa catcgtctgt      780
catatcatcg gggattccaa ctgcgcgttt gatgtcatcg agcctagaga tagcttcttc      840
tttggtgttg gaggttttgt caaggacttt aaaagcatcc ccgagacgac cctgaaggac      900
gagccaccga ggagactccg gcattgccaa cactccaatg ctaggaaaca ccgagggaac      960
cgctcctaca cctaacatga acctccatcc gaggtgctcg ggaagcttgg agaagaagta     1020
attggatacg tatcccaaaa gtataccaat attgataaaa atctgcatac aaaaatcaca     1080
ttatcatcat caacctccgt tatcatttcc aatcatacat aaaaaaaaa aaactttgga     1140 tcagttgaac ctcagggaaa gaggtaagga agcctcggga agaggcggga gcgacttcag     1200
cggtgtaaac aggcgcaatc atcatagcat aaccaacacc gataccggct acaaaacggc     1260
caaccattat gaaagggtag tttgtggcaa agcccattag tagggctccg caaaagaaga     1320
aggctcctgc caacactatt gtatatcgtc ttccgagcca atcagaagtt ctaccagctg     1380
cgccggaacc gaccagagag tagatgttta gaattcccat aagaatctca agttgtacat     1440
cagacagttt caaatcgtct tttatgaaaa ttgaagctcc actcatcact ccaatgtctg     1500
taacatcccc aaacatgtaa gaatgattat ctaaatcgta aaccaaacc aaatctgaat      1560 tgattgttaa tttaaaaaga agacgaaccg taaccaagga tgatagaagt catggaggct     1620
aagattgcac aagcaaaagc atatcggctt ctattccccc tcggtggctc tgactccgca     1680 atcacaaacac cttgttcaac tcccgaggaa ttcat                               1715
```

<210> SEQ ID NO 6
<211> LENGTH: 1722
<212> TYPE: DNA
<213> ORGANISM: Arabidopsis thaliana

<400> SEQUENCE: 6

```
atgagttcct caggagaaga acgaggtgtt gttgttgccg agtccgagcc gccaagaggg       60
aatagaagcc gatttgcttt tgcttgtgca atcttagcct ccatgacttc tatcatcctt      120
ggttatggtt ggtcttctaa tcattctcta acgatcaaat tcagatttg gtttggttta      180 acggtttaga taatcatcct cacattttat ggatgttgca gatattggag tgatgagtgg      240
agctgcaatt tcataaaag acgatttgaa gctgtcggac gtacaacttg agattcttat      300
gggaattcta aatatctatt ctctgatcgg ttcaggagca gctggaagaa cttccgattg      360
gatcggaaga cgatatacca tagtgttggc aggattcttc ttcttttgtg agccctact     420 aatgggtttt gccactaact atccttcat tatggtcggc cgttttgtag ccggtatcgg     480
tgtcggttac gctatgatga ttgcgcctgt ttataccacg gaagtcgctc cagcctcttc     540
tcgaggcttc cttagctctt tccctgaggt tcaatagatc caaattttac tagtttatat     600
gatataaaaa aaagaaaat taggtttata ttaatgtgat atgattttat atgcatgcag      660
```

| | |
|---|---|
| atatttatca acattggtat actattggga tacgtatcca attacttctt cgccaagctt | 720 |
| ccagagcaca ttggatggag gttcatgtta ggtattggag ctgtgccctc agtgtttcta | 780 |
| gccattggag tgttggcaat gcccgagtct ccacggtggc tcgtcatgca gggtcgtcta | 840 |
| ggggacgctt ttaaagtcct tgacaaaacc tcaaacacca agaagaagc catctcaagg | 900 |
| ctcaatgaca tcaaacgcgc agttggaatc cccgatgata tgacagacga tgttatagtc | 960 |
| gttccgaata aaagagcgc tggaaaaggc gtgtggaagg accttctcgt tcgaccaacc | 1020 |
| ccgtccgttc gacacatcct catagcatgc cttggtatcc atttctccca gcaagcctcc | 1080 |
| ggaattgatg ctgtcgtgct ttactctccg accatcttct caagggctgg actgaagtcc | 1140 |
| aagaatgacc agctcttggc tacggtcgct gtcggagttg tcaagactct cttcatcgta | 1200 |
| gtaggaactt gtttggtgga ccggtttgga cgtcgtgcct tgttgcttac gagtatgggt | 1260 |
| ggaatgtttt tttccttgac cgcccttgga actagtctca cggtgatcga caggaacccc | 1320 |
| gggcaaacac tcaagtgggc tatagggctc gccgttacga cggtgatgac ttttgtcgca | 1380 |
| acattctcat taggtgcagg ccccgtgacg tgggtctacg cctcagagat attccccgtg | 1440 |
| aggctaagag cgcaaggagc aagtttggga gtgatgttga atagactaat gagtggtatt | 1500 |
| ataggaatga cattcctatc tctttctaag ggtctcacca tcggtggtgc attccttctc | 1560 |
| ttcgccggag ttgcggttgc cgcgtgggtc ttcttcttca ctttcctccc ggagacacgt | 1620 |
| ggtgtgcctt tagaagaaat agagagtctc ttcgggagct acagcgcaaa caaaaagaac | 1680 |
| aatgttatga gcaaagggaa acaagtagtt gatgaacaat ga | 1722 |

<210> SEQ ID NO 7
<211> LENGTH: 1804
<212> TYPE: DNA
<213> ORGANISM: Arabidopsis thaliana

<400> SEQUENCE: 7

| | |
|---|---|
| tagacttagg tgcaaaagga agctgtcata tcggtggaaa tgtttcaact aatgctggtg | 60 |
| gtttgcgtct aatccgttat ggctcacttc atggaactgt attgggtaat gacttacagt | 120 |
| tttagttact ttcgatccat ctgaaaacat ttggatttca tgttctcatc attttttattt | 180 |
| tcttcatctc aggtctagaa gctgtcacag caaatggcaa cgtgcttgac atgcttggaa | 240 |
| ctttacgcaa agacaatact gggtacgact taaaacattt gtttattggt aggtattata | 300 |
| ttggcttgtg cttgtacaat gatttcaagt atcacttcat cagcaaaata gactaaatca | 360 |
| tcttgatttt ttctctttac tggtttccac aggtagtgaa ggatcacttg gtattgtaac | 420 |
| taaagtttct attctcacac aaccaaaatt gtcttctgta aatttagcct tcattgcttg | 480 |
| caaagattat ctcagctgcc aggtttaata caatttcttt tgtactcctg taattgaatt | 540 |
| ctatctacag aggagatagt gcgtgaactg ttatctctca ttgtgtttcc tttgtttgca | 600 |
| gaaacttctt gttgaagcaa agagaaatct tggagagata ctctcggctt cgagtttct | 660 |
| tgataacaat tccatggatt tggtaagctt ttaggaagtt actaatagga actgtttgca | 720 |
| ttcctgacac tttatcttgt gcacaaggct ttgattttgc taaacccttt ctgtttttaa | 780 |
| ttcattcaac aggtactgaa ccacctagac ggtgtacgta atccagtttc ctcttcggag | 840 |
| aacttttata ttctgatcga dacaacaggg agtgatgaaa ctaatgacag gtattgagaa | 900 |
| ttttctggtc tttctgtgac tttcacaatt ttccagtacc attt aaatga attctaagta | 960 |
| tttcagatcc cttgagagag tttttgtctg attcaaaaac taatgcaggg agaagcttga | 1020 |
| agcttttcctg ttgaagtcac tggaaaaagg tttagtttct gatggtgtaa tcgctcaaga | 1080 |

-continued

```
cattaaccag gcatcctcat tttggcgcat acgagaggta aaacacttga gagttatttc    1140
ctctgaaaaa gcttgatggt acacgacgaa taaagtcata atcataaccc tgcagggtat    1200
aacagaggcg ttacagaaag caggagctgt ttacaagtat gacttatcct taccggttga    1260
agaaatttac aatattgtta acgatcttcg agggagatta ggtaagatat atatcaatac    1320
attgtctcct aattacttga aaccgaaaga ttcaatgaaa actgcaacca atatgcaat    1380
gcttcaggtg acttagcaaa tgttatggga tatggtcacc ttggagacgg aaatctacat    1440
ttaaacatct cagccgcgga atataacgat aaggtaaaat tctgtatacc atatgaaaca    1500
ttccaagatg ttcaagtgat cattcattca ctcttttctt gcagctttta ggtttgatag    1560
agccttatgt ctatgagtgg acatcaaagc accgtggaag catcagtgcg aacatggat    1620
taggtgtaat gaaagctaat gaaatcttct acagcaaatc acccgaaact gtaagttaac    1680
aacaaacaac gtatggaaac tatgtataga actatcgtgt cactctattc ttaccggaat    1740
ataatattat gcaggttgca ttaatggctt ccattaaaaa gttgctggac ccaaagggaa    1800
ttct                                                                 1804

<210> SEQ ID NO 8
<211> LENGTH: 1662
<212> TYPE: DNA
<213> ORGANISM: Arabidopsis thaliana

<400> SEQUENCE: 8
ttatgagaaa cccccaatag agatggtttt agtttgaatc tcaagtccgt cacgatcacc      60
acgaggaccc ccaccaccaa aaagcttctc catctcctcc aatggcaatc ctttcgtctc     120
cggcaacata aagaagaaga accaccatgc cgccaccgct attccggcga atacgaagaa     180
cacgccccct gtcgtgatcg ccttcgtcat cgacagaaaa ctcattgaga ccgtcgcgtt     240
catgatccta ttaaccgcaa cacctatact cgctccctga gccctaagtc tcaacgggaa     300
tatctcggag ctgtacaccc atgtgatagg tccaagccct atggagaaaa aagctacaaa     360
tgcatacgta gagacgatgc ttaaaactcaa tgcccacgct aaccgcccaa atcgctgaac     420
catcgtgaga ctaaccgcta aactggtcaa tgcgaagacc atcccacccg tactggtcaa     480
caggagcttt ctacgaccta ccttgtcgag caagaaagtg gctattatta tgaaaaaggc     540
cttagttaaa cctacaccga ccgtggctag taagagcttg tctttcgaaa caactccggc     600
tttcttgaaa attctcgggc tgtacaacac gacggcctca atccccgtcg catgctcgaa     660
aaagtgtatc ccaacggccg ctatcaagat caaacgcacc gcaggtcgcg gttttatcac     720
caactccctc caaacacttt taccgtgatt cttcttctta acgccgccac caacttcttt     780
tatctctgtc acatctactt ccgcagcggt taagatgtct ctgaaccgtt cttcagcttc     840
ttcttccgta ttggatacca aaaccattat tttcttggct tcttctaacc taccttgcat     900
cacaagccac ctcggcgact cgggcattct tgtaatccca aaagccaata tcaaagacgg     960
gaacgctgcg attccaagca tcaatctcca tccaagtttc aacgtcagtt tcccaaaaca    1020
gtaattcgag acatagccta gtaaaatccc aagactaata caaagctcag gtagagaagt    1080
gagaaagcct ctatgtgacg cagaggatat ctcggcagag taaaccggag ctatcatgag    1140
agcaaaccct acaccaactc cggcaataca tcgtccgacc atcaaaacag gatagtttgg    1200
gccgtaaccc ataagaactg agcccactaa gaatatcacg gcggagagag ctatggtgta    1260
acgtcggccg atgacgtcag acgttttccc cgccgttagt gatccgacga gtgcacaaag    1320
```

| | |
|---|---|
| attcaagatt ccggccaaaa cttcaatctg agtgtcgttt atttttagat catctcttat | 1380 |
| aaatatctga gctccgctca taactcccgt atctaaggac aacacaccat acaaaaaaa | 1440 |
| aaaatattcg ttaatataaa atcattaata taattccatt gaatatatct ttatatgata | 1500 |
| tatgtagaaa acttttgttt gatatgtaga gaatgttagt atgttaccat atccaaagat | 1560 |
| gatagaaatg atggaagcaa caatggcaca cccgaaagcg aacttgttca tatgagggtt | 1620 |
| tggatccgaa ccgggaaaat tatgaccatc agcatgaacc at | 1662 |

<210> SEQ ID NO 9
<211> LENGTH: 1690
<212> TYPE: DNA
<213> ORGANISM: Arabidopsis thaliana

<400> SEQUENCE: 9

| | |
|---|---|
| tcaaaactcc tgttccttgc gcacaagacg ctcagcatct ccaagctcaa cttcaccgtc | 60 |
| tttctttcc agcccaccct gaaacatcaa ctctatctgc tccagtgact tcccgcttgt | 120 |
| ctcggggact agcacataca cgaagataac tgagagtgca gacacgaggg agaaaacgaa | 180 |
| gaaggttcct ccaacagtga tggcacgtga cacagagagg aaggacatgg ccaccagacc | 240 |
| gctgcacacc ctgttcccaa ccgccccaag cgcagatgcc tgggctctta atcgtaatgg | 300 |
| aaagatctct gatgtcaaga cccagcaaac aggtcccatt cctatggaga agaaggcaac | 360 |
| gtttccacaa acaaagagaa gcgccaaggt tatcccaagc gttccttggc cgaggaatgt | 420 |
| gagcgtaaag cttagacaaa agagacacag agtcattcct attgtgctca cataaagcag | 480 |
| cggtttccgg ccaacactat caatcaggaa ggtggcaaat agtatgaaca ctgttttcgt | 540 |
| gacaccaaca gcgacagttg cagcgagcag tttggtctcg tcttgtatcc cagcctcttt | 600 |
| caggatctct ggactatagt agactgtggc gtcaattcct gtgatctgct ggaaacactg | 660 |
| gattccaaat ccaacaatca gcattttccg tacaacagga gatgggctaa gaagctcacg | 720 |
| ccacacgggc ctgtcctcgc tgccttctgt atgtgcagcc gccagttgta tctctgcaag | 780 |
| ccgctcttcc gcttcgtcat ctcgctcatt cgttttcatg agcacctctc gtgcactgtc | 840 |
| cactcggcct ttcatcacca gccacctcgg cgactcaggg atcacacaca gcgcaaatcc | 900 |
| tatgaacacc gaaggaagaa tcccaactgc aagcatgatc ctccagctga tatgcacgga | 960 |
| aagccccgag aaagcgtagt tcgaaacata gcccagcaag atccctagat ttatgaagat | 1020 |
| ctcagggaac gaagtgaaaa atcctctagc tacggtgggg gatatctcgg cgatgtagac | 1080 |
| aggagcgatc atgacaccaa gcccaatccc aatgccggct aaagttctcc ctatcatcaa | 1140 |
| aacctcgaaa gacggagcga cagccatcac ggcagcacca gtctggaaga cgagagcagc | 1200 |
| caaggccatg gtccattttc taccgataga gtcagaggtt ctgccgccgg ctaagctgcc | 1260 |
| aaagagtgag atgatgctaa ggctaccaat gagcacttcc gtctgcacct ccgttatttt | 1320 |
| gagatcctgc tgtatgaaca acaccgcacc gctcattacc ccaacatctg acaaatacca | 1380 |
| aaaacagagc acacatacct ttttgtaagt caacaaagta agaagaaga agaagaatcc | 1440 |
| gattatataa gtaaaaccga ccgtagccga gaagaacatt gttcaaggat gcaaaaaagg | 1500 |
| cacaagccat aacgtatttt ctggttctac tgtttctagc ctctgcttca cgatgattct | 1560 |
| gcgattcctc cgcgtcggag tccattctct gatacttatt cttcttattt ccgcagaga | 1620 |
| ccgccggaaa acccgagcca ccgccattac caacctccgg aagattcttc atcatctccc | 1680 |
| tccgccgagg | 1690 |

<210> SEQ ID NO 10
<211> LENGTH: 1518
<212> TYPE: DNA
<213> ORGANISM: Bacillus subtilis

<400> SEQUENCE: 10

```
aagggagtca tctttatgaa aaagcagtca aatatatggc tttattttt cggagctctt       60
ggaggcgcgt tatatggcta tgataccgga gtgatttccg gagctatttt atttatgaaa     120
aaggagttag gcttaaacgc gtttacagaa ggtcttgttg tcagctcctt gctggttggg     180
gcgatattgg gctcaggagc ggccggcaag ctgactgacc gtttcggaag aaaaaaagca     240
attatggcag ccgcgctgct gttttgtata ggcggtcttg gtgtggcact ggccccaaat     300
acaggagtca tggtgctgtt tcgcatcatt ttgggacttg cagtcggaac atcgacgaca     360
atcgtacccc tttatttatc tgaactggcg ccaaaacata aacgcggggc gctgtcatca     420
ctgaatcagc tgatgatcac ggtcggcatc cttctttctt acattgtcaa ttacatattt     480
gccgatgccg aagcgtggcg ctggatgctt ggattggctg ctgtgccgtc attgctcttg     540
cttattggca ttttgtttat gccggagagc ccgcgctggc tgttcacgaa tggcgaagaa     600
agcaaagcga agaaaattct tgaaaaattg cgtggcacaa agatattga tcaggaaata      660
catgatataa agaagcgga aaagcaggat gaaggcggtc tgaaggagct gttcgatcca      720
tgggtgcgcc cagcgcttat tgcaggtttg ggactcgctt ttttgcagca atttatcgga     780
acgaatacga tcatctacta tgcgccaaag acctttacaa acgtcggatt cggaaactcc     840
gcttcgattt taggcacggt cggaatcggc acagtcaatg ttctcatgac attagtagcg     900
attaaaatca tcgacaagat tggaagaaag ccgttactgc tattcgggaa tgcgggcatg     960
gtgatcagct tgatcgttct cgctttagta aatctctttt tcaataacac tccggctgcc    1020
tcatggacga ccgtcatttg tttaggcgtg tttatcgttg tctttgcggt cagctgggga    1080
ccggttgtgt gggtgatgct tcctgaattg ttcccgcttc acgtcagagg aatcgggacc    1140
ggtgtttcga ccttaatgtt gcacgttggg acactgattg tttcattaac ctatccaata    1200
ttaatggaag cgatcggaat cagttattta ttcctgattt atgccgcgat cggtatcatg    1260
gcgttcttat ttgtccgatt taaagtgaca gagacaaagg gaagaagcct tgaagaaatt    1320
gagcaggatt tacgggacaa aaacggacag ggaggagcgg ccggaaaaca gcagactgtc    1380
ggaacataaa aaagggtgcg cgatcatgcg cacccttttg attgcttact ttcccaccgt    1440
gccaaagtta atgatttaa aagaaatatc gtacttaaaa tcagtctcag aaaatatttc    1500
atcccaatgc cctttac                                                   1518
```

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: peptide
      fragment from the Apium graveolens AgMaT1 protein

<400> SEQUENCE: 11

Ala Cys Ala Leu Leu Ala Ser Met Asn Ser Ile Leu Leu Gly Tyr Asp
 1               5                  10                  15

Thr Gly Val Leu Ser Gly Ala Ser Ile
            20                  25

<210> SEQ ID NO 12
<211> LENGTH: 21

```
<212> TYPE: PRT
<213> ORGANISM: Artificial Sequence
<220> FEATURE:
<223> OTHER INFORMATION: Description of Artificial Sequence: peptide
      fragment from the Apium graveolens AgMaT1 protein

<400> SEQUENCE: 12

Gln Ile Glu Ile Ile Ile Gly Ile Ile Asn Ile Tyr Ser Leu Leu Gly
 1               5                  10                  15

Ser Ala Ile Ala Gly
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: peptide
      fragment from the Apium graveolens AgMaT1 protein

<400> SEQUENCE: 13

Tyr Thr Met Val Leu Ala Gly Ile Ile Phe Phe Leu Gly Ala Ile Phe
 1               5                  10                  15

Met Gly Leu Ala
            20

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: peptide
      fragment from the Apium graveolens AgMaT1 protein

<400> SEQUENCE: 14

Phe Leu Met Phe Gly Arg Phe Val Ala Gly Ile Gly Val Gly Tyr Ala
 1               5                  10                  15

Met Met Ile Ala Pro Val Tyr Thr Ala
            20                  25

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: peptide
      fragment from the Apium graveolens AgMaT1 protein

<400> SEQUENCE: 15

Phe Leu Thr Ser Phe Pro Glu Val Phe Ile Asn Ser Gly Val Leu Leu
 1               5                  10                  15

Gly Tyr Val Ser Asn Phe Ala Phe Ala
            20                  25

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: peptide
      fragment from the Apium graveolens AgMaT1 protein

<400> SEQUENCE: 16

Ile Met Leu Gly Ile Gly Ala Phe Pro Ser Val Ala Leu Ala Ile Ile
 1               5                  10                  15
```

Val Leu Tyr Met
            20

<210> SEQ ID NO 17
<211> LENGTH: 22
<212> TYPE: PRT
<213> ORGANISM: Artificial Sequence
<220> FEATURE:
<223> OTHER INFORMATION: Description of Artificial Sequence: peptide
      fragment from the Apium graveolens AgMaT1 protein

<400> SEQUENCE: 17

Ala Ala Ile Thr Gly Ile Gly Ile His Phe Phe Gln Gln Ala Cys Gly
  1               5                  10                  15

Ile Asp Ala Val Val Leu
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: peptide
      fragment from the Apium graveolens AgMaT1 protein

<400> SEQUENCE: 18

Leu Leu Ala Thr Ile Ala Val Gly Val Cys Lys Thr Val Phe Ile Leu
  1               5                  10                  15

Ile Ser Thr Phe
            20

<210> SEQ ID NO 19
<211> LENGTH: 22
<212> TYPE: PRT
<213> ORGANISM: Artificial Sequence
<220> FEATURE:
<223> OTHER INFORMATION: Description of Artificial Sequence: peptide
      fragment from the Apium graveolens AgMaT1 protein

<400> SEQUENCE: 19

Leu Met Leu Thr Ser Met Gly Gly Met Val Ile Ala Leu Phe Val Leu
  1               5                  10                  15

Ala Gly Ser Leu Thr Val
            20

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: peptide
      fragment from the Apium graveolens AgMaT1 protein

<400> SEQUENCE: 20

Gly Gly Leu Ala Ile Phe Thr Val Tyr Ala Phe Val Ser Ile Phe Ser
  1               5                  10                  15

Ser Gly Met Gly Pro Ile Ala Trp Val Tyr
            20                  25

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: peptide
      fragment from the Apium graveolens AgMaT1 protein

```
<400> SEQUENCE: 21

Cys Ser Ile Gly Val Ala Val Asn Arg Gly Met Ser Gly Ile Ile Gly
 1               5                  10                  15

Met Thr Phe Ile Ser
            20

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: peptide
      fragment from the Apium graveolens AgMaT1 protein

<400> SEQUENCE: 22

Ala Phe Leu Leu Phe Ala Val Val Ala Ser Ile Gly Trp Val Phe Met
 1               5                  10                  15

Tyr Thr Met Phe
            20

<210> SEQ ID NO 23
<211> LENGTH: 75
<212> TYPE: DNA
<213> ORGANISM: Artificial Sequence
<220> FEATURE:
<223> OTHER INFORMATION: Description of Artificial Sequence: fragment
      of the nucleotide sequence coding for the
      AgMaT1 protein from Apium graveolens
<220> FEATURE:
<221> NAME/KEY: CDS
<222> LOCATION: (1)..(75)

<400> SEQUENCE: 23 gct tgt gct ctt tta gct tcc atg aat tcc atc tta ctc ggc tat gac      48
Ala Cys Ala Leu Leu Ala Ser Met Asn Ser Ile Leu Leu Gly Tyr Asp
 1               5                  10                  15 acc gga gtg ttg agt gga gca tca ata                                  75
Thr Gly Val Leu Ser Gly Ala Ser Ile
            20                  25

<210> SEQ ID NO 24
<211> LENGTH: 63
<212> TYPE: DNA
<213> ORGANISM: Artificial Sequence
<220> FEATURE:
<223> OTHER INFORMATION: Description of Artificial Sequence: fragment
      of the nucleotide sequence coding for the
      AgMaT1 protein from Apium graveolens
<220> FEATURE:
<221> NAME/KEY: CDS
<222> LOCATION: (1)..(63)

<400> SEQUENCE: 24 caa atc gaa ata atc atc gga atc atc aac atc tac tct ctt ctt ggt      48
Gln Ile Glu Ile Ile Ile Gly Ile Ile Asn Ile Tyr Ser Leu Leu Gly
 1               5                  10                  15 tcg gcc ata gcc gga                                                  63
Ser Ala Ile Ala Gly
            20

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: fragment
``` of the nucleotide sequence coding for the
      AgMaT1 protein from Apium graveolens
<220> FEATURE:
<221> NAME/KEY: CDS
<222> LOCATION: (1)..(60)

<400> SEQUENCE: 25 tac acc atg gta cta gct ggt atc ata ttt ttt cta gga gcc att ttc    48
Tyr Thr Met Val Leu Ala Gly Ile Ile Phe Phe Leu Gly Ala Ile Phe
  1               5                  10                  15 atg ggg ctt gct                                                    60
Met Gly Leu Ala
            20

<210> SEQ ID NO 26
<211> LENGTH: 75
<212> TYPE: DNA
<213> ORGANISM: Artificial Sequence
<220> FEATURE:
<223> OTHER INFORMATION: Description of Artificial Sequence: fragment
      of the nucleotide sequence coding for the
      AgMaT1 protein from Apium graveolens
<220> FEATURE:
<221> NAME/KEY: CDS
<222> LOCATION: (1)..(75)

<400> SEQUENCE: 26 ttt ctc atg ttt ggt cgc ttt gtt gct gga att ggt gtc ggt tat gcc    48
Phe Leu Met Phe Gly Arg Phe Val Ala Gly Ile Gly Val Gly Tyr Ala
  1               5                  10                  15 atg atg atc gct ccc gtc tac act gcc                                75
Met Met Ile Ala Pro Val Tyr Thr Ala
            20                  25

<210> SEQ ID NO 27
<211> LENGTH: 75
<212> TYPE: DNA
<213> ORGANISM: Artificial Sequence
<220> FEATURE:
<223> OTHER INFORMATION: Description of Artificial Sequence: fragment
      of the nucleotide sequence coding for the
      AgMaT1 protein from Apium graveolens
<220> FEATURE:
<221> NAME/KEY: CDS
<222> LOCATION: (1)..(75)

<400> SEQUENCE: 27 ttc ctc act tct ttt cct gag gtt ttc att aat tct ggt gtg ttg ctc    48
Phe Leu Thr Ser Phe Pro Glu Val Phe Ile Asn Ser Gly Val Leu Leu
  1               5                  10                  15 ggg tat gta tcc aac ttt gca ttt gcc                                75
Gly Tyr Val Ser Asn Phe Ala Phe Ala
            20                  25

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: fragment
      of the nucleotide sequence coding for the
      AgMaT1 protein from Apium graveolens
<220> FEATURE:
<221> NAME/KEY: CDS
<222> LOCATION: (1)..(60)

<400> SEQUENCE: 28 att atg ctg gga att gga gca ttt cct tca gtt gcc ttg gcc ata att    48
Ile Met Leu Gly Ile Gly Ala Phe Pro Ser Val Ala Leu Ala Ile Ile

```
                1               5                      10                      15
gtg tta tat atg                                                                          60
Val Leu Tyr Met
            20

<210> SEQ ID NO 29
<211> LENGTH: 66
<212> TYPE: DNA
<213> ORGANISM: Artificial Sequence
<220> FEATURE:
<223> OTHER INFORMATION: Description of Artificial Sequence: fragment
      of the nucleotide sequence coding for the
      AgMaT1 protein from Apium graveolens
<220> FEATURE:
<221> NAME/KEY: CDS
<222> LOCATION: (1)..(66)

<400> SEQUENCE: 29 gct gca att acg ggt att ggt att cat ttc ttc caa cag gct tgt ggt      48
Ala Ala Ile Thr Gly Ile Gly Ile His Phe Phe Gln Gln Ala Cys Gly
  1               5                  10                  15 att gat gct gtt gtt tta                                              66
Ile Asp Ala Val Val Leu
            20

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: fragment
      of the nucleotide sequence coding for the
      AgMaT1 protein from Apium graveolens
<220> FEATURE:
<221> NAME/KEY: CDS
<222> LOCATION: (1)..(60)

<400> SEQUENCE: 30 ctc ctt gcg aca att gct gtt gga gtc tgc aaa aca gtc ttt att ctg      48
Leu Leu Ala Thr Ile Ala Val Gly Val Cys Lys Thr Val Phe Ile Leu
  1               5                  10                  15 ata tca acg ttt                                                      60
Ile Ser Thr Phe
            20

<210> SEQ ID NO 31
<211> LENGTH: 66
<212> TYPE: DNA
<213> ORGANISM: Artificial Sequence
<220> FEATURE:
<223> OTHER INFORMATION: Description of Artificial Sequence: fragment
      of the nucleotide sequence coding for the
      AgMaT1 protein from Apium graveolens
<220> FEATURE:
<221> NAME/KEY: CDS
<222> LOCATION: (1)..(66)

<400> SEQUENCE: 31 ctg atg cta aca agt atg ggg ggt atg gtt att gct cta ttt gta ctg      48
Leu Met Leu Thr Ser Met Gly Gly Met Val Ile Ala Leu Phe Val Leu
  1               5                  10                  15 gca ggc tca ttg acg gtt                                              66
Ala Gly Ser Leu Thr Val
            20

<210> SEQ ID NO 32
<211> LENGTH: 78
<212> TYPE: DNA
```

```
<213> ORGANISM: Artificial Sequence
<220> FEATURE:
<223> OTHER INFORMATION: Description of Artificial Sequence: fragment
      of the nucleotide sequence coding for the
      AgMaT1 protein from Apium graveolens
<220> FEATURE:
<221> NAME/KEY: CDS
<222> LOCATION: (1)..(78)

<400> SEQUENCE: 32 ggt ggt ttg gca ata ttt aca gtg tat gct ttt gtg tcg ata ttt tca      48
Gly Gly Leu Ala Ile Phe Thr Val Tyr Ala Phe Val Ser Ile Phe Ser
 1               5                  10                  15 agt ggc atg ggt cca att gct tgg gtc tat                              78
Ser Gly Met Gly Pro Ile Ala Trp Val Tyr
            20                  25

<210> SEQ ID NO 33
<211> LENGTH: 63
<212> TYPE: DNA
<213> ORGANISM: Artificial Sequence
<220> FEATURE:
<223> OTHER INFORMATION: Description of Artificial Sequence: fragment
      of the nucleotide sequence coding for the
      AgMaT1 protein from Apium graveolens
<220> FEATURE:
<221> NAME/KEY: CDS
<222> LOCATION: (1)..(63)

<400> SEQUENCE: 33 tgt agt atc gga gtg gca gtt aac cgt ggc atg agt ggc ata att gga      48
Cys Ser Ile Gly Val Ala Val Asn Arg Gly Met Ser Gly Ile Ile Gly
 1               5                  10                  15 atg aca ttt ata tcg                                                  63
Met Thr Phe Ile Ser
            20

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence: fragment
      of the nucleotide sequence coding for the
      AgMaT1 protein from Apium graveolens
<220> FEATURE:
<221> NAME/KEY: CDS
<222> LOCATION: (1)..(60)

<400> SEQUENCE: 34 gca ttc ctt tta ttt gct gtg gtt gca tct atc gga tgg gtc ttt atg      48
Ala Phe Leu Leu Phe Ala Val Val Ala Ser Ile Gly Trp Val Phe Met
 1               5                  10                  15 tac aca atg ttc                                                      60
Tyr Thr Met Phe
            20

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: synthetic
      primer

<400> SEQUENCE: 35
gactcgagat gacaaaatca gacgaaacaa c                                   31
```

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: synthetic
      primer

<400> SEQUENCE: 36
gaagatcttc acacttggtc taaaatttcc                                      30

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: synthetic
      primer
<220> FEATURE:
<221> NAME/KEY: modified_base
<222> LOCATION: (3)
<223> OTHER INFORMATION: a, t, c or g
<220> FEATURE:
<221> NAME/KEY: modified_base
<222> LOCATION: (6)
<223> OTHER INFORMATION: a, t, c or g
<220> FEATURE:
<221> NAME/KEY: modified_base
<222> LOCATION: (12)
<223> OTHER INFORMATION: a, t, c or g
<220> FEATURE:
<221> NAME/KEY: modified_base
<222> LOCATION: (15)
<223> OTHER INFORMATION: a, t, c or g
<220> FEATURE:
<221> NAME/KEY: modified_base
<222> LOCATION: (18)
<223> OTHER INFORMATION: a, t, c or g

<400> SEQUENCE: 37
ccnacnccra anggnarnar                                                 20

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 38

Leu Leu Gly Phe Gly Val Gly
 1               5

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: synthetic
      dC primer

<400> SEQUENCE: 39
cccccccccc cccccc                                                     16

<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence: synthetic -continued dG primer

<400> SEQUENCE: 40
gggggggggg gggggg                                                        16

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: synthetic
      primer

<400> SEQUENCE: 41
attctggtgt gttgctcg                                                  18

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: synthetic
      primer

<400> SEQUENCE: 42
caatgaacag tatgatgtg                                             19

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 43

Pro Glu Ser Pro Arg
  1             5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 44

Pro Glu Thr Lys Gly
  1             5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MOD_RES
<222> LOCATION: (6)
<223> OTHER INFORMATION: variable amino acid

<400> SEQUENCE: 45

Pro Glu Ser Pro Arg Xaa Leu
  1             5

```
<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MOD_RES
<222> LOCATION: (7)..(9)
<223> OTHER INFORMATION: variable amino acid

<400> SEQUENCE: 46

Pro Glu Thr Gln Gly Arg Xaa Xaa Xaa Glu
 1               5                  10
```